(12) United States Patent
Galleguillos et al.

(10) Patent No.: US 9,579,272 B2
(45) Date of Patent: Feb. 28, 2017

(54) ALKYL GLYCOSIDE-BASED MICELLAR THICKENERS FOR SURFACTANT SYSTEMS

(71) Applicant: Lubrizol Advanced Materials, Inc., Cleveland, OH (US)

(72) Inventors: Ramiro Galleguillos, Hudson, OH (US); Anchuu Wu, Broadview Heights, OH (US)

(73) Assignee: Lubrizol Advanced Materials, Inc.

( * ) Notice: Subject to any disclaimer, the term of this patent is extended or adjusted under 35 U.S.C. 154(b) by 28 days.

(21) Appl. No.: 14/432,925

(22) PCT Filed: Jun. 5, 2013

(86) PCT No.: PCT/US2013/044198
§ 371 (c)(1),
(2) Date: Apr. 1, 2015

(87) PCT Pub. No.: WO2013/188183
PCT Pub. Date: Dec. 19, 2013

(65) Prior Publication Data
US 2016/0022557 A1 Jan. 28, 2016

Related U.S. Application Data

(60) Provisional application No. 61/660,206, filed on Jun. 15, 2012.

(51) Int. Cl.
*A61K 8/60* (2006.01)
*A61Q 5/02* (2006.01)
*C11D 3/22* (2006.01)
*A61Q 19/10* (2006.01)

(52) U.S. Cl.
CPC .............. *A61K 8/602* (2013.01); *A61Q 5/02* (2013.01); *A61Q 19/10* (2013.01); *C11D 3/226* (2013.01); *A61K 2800/48* (2013.01)

(58) Field of Classification Search
CPC ....................................................... A61K 8/60
USPC ...................................................... 510/123
See application file for complete search history.

(56) References Cited

U.S. PATENT DOCUMENTS

| | | | | | |
|---|---|---|---|---|---|
| 3,597,417 | A | * | 8/1971 | Myhre | C07H 15/04 536/119 |
| 4,450,090 | A | * | 5/1984 | Kinney | A61K 8/466 510/124 |
| 4,687,843 | A | * | 8/1987 | Smolin | A61K 8/39 514/845 |
| 4,840,815 | A | * | 6/1989 | Meyer | A23D 7/011 426/601 |
| 5,200,328 | A | * | 4/1993 | Kirk | A61K 8/602 435/101 |
| 5,502,175 | A | * | 3/1996 | Desai | A61K 8/602 536/115 |
| 5,550,220 | A | * | 8/1996 | Meyer | A23D 7/011 426/106 |
| 5,939,081 | A | * | 8/1999 | Ansmann | A61K 8/06 424/401 |
| 2002/0123625 | A1 | * | 9/2002 | Polovsky | A61K 8/608 536/120 |
| 2016/0022557 | A1 | * | 1/2016 | Galleguillos | C11D 3/226 510/123 |

FOREIGN PATENT DOCUMENTS

DE 4015733 A1 * 11/1991 ............. A61K 8/604
EP 1329255 A1 * 7/2003 .......... B01F 17/0021

* cited by examiner

Primary Examiner — Nicole M Buie-Hatcher
Assistant Examiner — M. Reza Asdjodi
(74) Attorney, Agent, or Firm — Thoburn T. Dunlap; Teresan W. Gilbert; Ann M. Skerry

(57) ABSTRACT

A rheology modifier which includes a mixture of short and long chain fatty acid esters is suitable for use in liquid surfactant-based compositions. A surfactant-based composition includes a surfactant, the rheology modifier, and water. The rheology modifier includes a mixture of alkyl glycoside fatty acid esters including a long chain fatty acid ester of an alkyl glycoside and a short chain fatty acid ester of an alkyl glycoside. The long chain fatty acid ester includes at least one fatty acid residue: $R^1(O)O$—, wherein $R^1$ is a $C_{12}$ or higher hydrocarbon. The short chain fatty acid ester includes least one fatty acid residue: $R^2(O)O$—, wherein $R^2$ is a $C_6$-$C_{10}$ hydrocarbon.

63 Claims, 1 Drawing Sheet

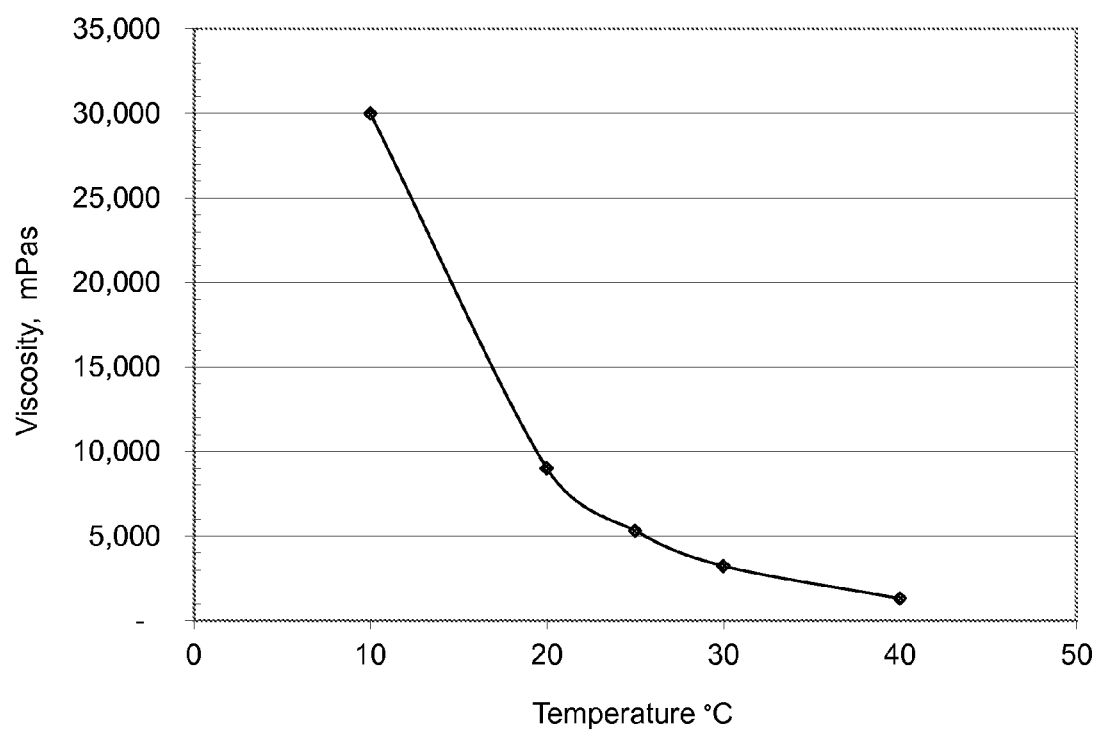

ALKYL GLYCOSIDE-BASED MICELLAR THICKENERS FOR SURFACTANT SYSTEMS

CROSS REFERENCE TO RELATED APPLICATION

This application claims priority from PCT Application Serial No. PCT/US2013/044198 filed on Jun. 5, 2013, which claims the benefit of U.S. Provisional Application No. 61/660,206 filed on Jun. 15, 2012.

FIELD OF INVENTION

The present embodiment relates to rheology modifiers and finds particular application in connection with an esterified glycoside compound and a surfactant-based composition which includes the compound.

BACKGROUND

Liquid aqueous compositions containing surfactants, such as shampoos, liquid soaps, body washes, facial cleansers, other personal care, pharmaceutical and industrial products, typically contain thickeners in order to increase the viscosity of the liquid composition. This enables convenient delivery and handling of the formulated product.

Traditional thickeners which have been used in such compounds include a diversity of anionic, cationic and nonionic synthetic polymers, such as carboxylated and quaternized polyacrylates and polyvinyl compounds. Typical nonionic synthetic polymers include polyvinylpyrrolidone, polyethylene glycol (PEG), and alkoxylated polyols containing lipophilic substituents, such as PEG150 distearate, and ethoxylated methyl glucoside esterified with a fatty acids. Other thickeners which have been used include naturally derived anionic and cationic gums, such as chemically modified cellulose, xanthan gum, tara gum, and guar gum, and a variety of inorganic clays, salts, and electrolytes. A comprehensive list of rheology modifiers is found in the International Cosmetic Ingredient Dictionary and Handbook by T. Gottschalk and H. P. Breslawec, "International Cosmetic Ingredient Dictionary and Handbook," pages 3974-3977, 14th Edn, Personal Care Products Council Publisher, Washington, D.C., USA (2012). Additional information regarding the physical and chemical mechanisms through which the different thickeners confer viscosity to surfactant compositions is discussed in E. Desmond Goddard, "Principles of Polymer Science and Technology in Cosmetics and Personal Care," Cosmetic Science and Technology, 1 edition (Mar. 10, 1999), Informa HealthCare, and in "Polymers in Aqueous Media—Performance through Association," J. E. Glass, Editor, Advances in Chemistry Series No, 223, American Chemical Society, Washington D.C. (1989).

One group of nonionic thickeners includes relatively low molecular weight compounds of various types, such as nonionic alkoxylated surfactants, aliphatic amides, fatty alcohols, hydrophobically modified alkoxylated molecules, which are able to provide increased viscosity to liquid surfactant-based compositions. The mechanism through which these compounds increase the viscosity of aqueous surfactant compositions is thought to be by selective association with the surfactant micelles themselves. These compounds are often referred to as associative thickeners or micellar thickeners because they thicken through association with a surfactant, perhaps through hydrophobic or lipophilic substituents on these small molecules.

Preparation of fatty acid modified, alkoxylated polymers using sugar polyols is disclosed, for example, in U.S. Pat. Nos. 4,252,826; 4,264,478; 4,323,468; 4,324,703; 4,364,930; 4,687,843; 4,708,813; 5,744,062; 6,320,065; 6,727,357; 6,808,701 and 7,297,667 and European patent EP1329255. Alkoxylated glycoside polymers that have been hydrophobically modified with a variety of hydrocarbons are disclosed, for example, in U.S. Pub. Nos. 20010051142; 20020123625; 20020165104; 20030095942; 20030108506; 20030130162; 20030158065; 20030181715; 20030194387; 20040048766; 20040057921; 20040062730; 20040081632; 20040086470; 20040136943; 20050164896; and 20060019861.

One problem with using such compounds as thickeners is that they tend to have characteristics which make them less attractive for use in human personal care products. For example, they are typically prepared from petroleum-derived precursors, and as such are not considered to be environmentally acceptable or renewable materials. In addition, a number of them are ethoxylated compounds. Due to the presence of residual dioxane in the product as result of the preparation procedure, there is a concern about their toxicity. Similarly, aliphatic amines, such as cocamide-DEA and others, can contain residual amines that are believed to form nitrosamines during the shelf life of the product, which are considered to be carcinogens. These conventional thickeners therefore may be unsuited to use in aqueous surfactant-based liquid cleansing compositions for personal care, where the desire is to have as high a concentration as possible of naturally derived or renewable ingredients.

The esterification of polyols, such as sugars or saccharides such as glucose, mannose, galactose, fructose, sucrose, maltose, lactose, starch, cellulose and their derivatives including sorbitol, sorbitane and alkyl polyglucoside, has been studied. Examples of fatty acid esters formed from these sugars are disclosed in PCT applications WO/1992/003060 and WO/2004/031244, where the resulting esters are complex mixtures of polyesters which are used as fat substitutes in food products. As potential thickener components of a surfactant-based personal care composition, however, these esterified materials have some disadvantages. The polyols themselves are typically mixtures of various unstable sugars. Hence, the quality of the resulting esterified product tends to be poor. In addition, the polyol tends to decompose, undergoing significant forms of rearrangement during esterification at temperatures above 130° C., including oligomerization, caramelization or even charring. This results in discolored, dark products containing significant levels of polysaccharides and other intractable species. To address the instability of these common sugars, catalytic enzymes have been proposed, which allow the esterification to be effected under milder reaction conditions, as disclosed in EP 0 507 323. However, the yields of esters using enzymes as catalysts tend to be very low, making them unsuitable for commercial production of such compounds.

U.S. Pub. No. 20120015893 and EP 2 415 454 A1, for example, disclose esters of sorbitan, such as sorbitan sesquicaprylate, in a cleansing composition, such as a shampoo. US Pub. No. 20110092405 discloses surfactant compositions for cleansing formulations thickened with fatty acid esters of glycerol. Both of these polyols suffer from some stability problems.

US Pub. No. 20060024256 discloses the use of fatty amphiphiles in surfactant compositions, but requires the amphiphiles to be incorporated into a dispersed gel network phase to be effective.

The exemplary embodiment provides a micellar thickener suitable as a rheology modifier in surfactant-based compositions.

BRIEF DESCRIPTION

In accordance with one aspect of the exemplary embodiment, a composition includes a surfactant, a rheology modifier, and water. The rheology modifier includes a mixture of alkyl glycoside fatty acid esters including a long chain fatty acid ester of an alkyl glycoside and a short chain fatty acid ester of an alkyl glycoside. The long chain fatty acid ester consists of at least one fatty acid ester group or fatty acid residue: $R^1(O)O$—, wherein $R^1$ is a $C_{12}$ or higher hydrocarbon. The short chain fatty acid ester consists of least one fatty acid ester group or fatty acid residue: $R^2(O)O$—, wherein $R^2$ is a $C_6$-$C_{10}$ hydrocarbon.

In another aspect, a method of forming a composition includes combining a rheology modifier with an anionic surfactant and water. The rheology modifier includes a mixture of alkyl glycoside fatty acid esters including a long chain fatty acid ester of an alkyl glycoside and a short chain fatty acid ester of an alkyl glycoside. The long chain fatty acid ester consists of at least one fatty acid ester group or fatty acid residue: $R^1(O)O$—, wherein $R^1$ is a $C_{12}$ or higher hydrocarbon. The short chain fatty acid ester consists of least one fatty acid ester group or fatty acid residue: $R^2(O)O$—, wherein $R^2$ is a $C_6$-$C_{10}$ hydrocarbon.

In another aspect, a rheology modifier includes a mixture of alkyl glycoside fatty acid esters, including a long chain fatty acid ester of an alkyl glycoside, the long chain fatty acid ester consisting of at least one fatty acid ester group or fatty acid residue: $R^1(O)O$—, wherein $R^1$ is a $C_{12}$-$C_{23}$ hydrocarbon group, and a short chain fatty acid ester of an alkyl glycoside, the short chain fatty acid ester consisting of least one fatty acid ester group or fatty acid residue: $R^2(O)O$—, wherein $R^2$ is a $C_6$-$C_{10}$ hydrocarbon group. A ratio of $R^1(O)O$— to $R^2(O)O$— in the rheology modifier is from 0.2:1 to 0.7:1.

In another aspect, a composition includes a rheology modifier derived from a reaction of an alkyl glycoside with a long chain fatty acid or derivative thereof and a short chain fatty acid or derivative thereof, the short and long chain fatty acids or derivatives thereof including a hydrocarbon chain of at least 6 carbons in length, and wherein the short and long chain fatty acids or derivatives thereof differ in the length of their respective hydrocarbon chains by an average of at least 6 carbon atoms.

In still another aspect, selected non-limiting embodiments of the invention are as follows:

EMBODIMENT 1

A composition comprising:
a surfactant;
a rheology modifier comprising a mixture of alkyl glycoside fatty acid esters comprising:
  a long chain fatty acid ester of an alkyl glycoside, the long chain fatty acid ester consisting of at least one fatty acid ester group $R^1(O)O$—, wherein $R^1$ is a $C_{12}$ or higher hydrocarbon, and
  a short chain fatty acid ester of an alkyl glycoside, the short chain fatty acid ester consisting of least one fatty acid ester group $R^2(O)O$—, wherein $R^2$ is a $C_6$-$C_{10}$ hydrocarbon; and
water.

EMBODIMENT 2

The composition of embodiment 1, wherein in the long chain fatty acid ester $R^1$ is a $C_{12}$-$C_{23}$ hydrocarbon.

EMBODIMENT 3

The composition of any of the preceding embodiments, wherein in the long chain fatty acid ester, $R^1$ is a $C_{13}$ or higher hydrocarbon.

EMBODIMENT 4

The composition of any of the previous embodiments, wherein the long chain fatty acid comprises at least one fatty acid ester in which $R^1$ is a $C_{18}$ hydrocarbon.

EMBODIMENT 5

The composition of any of the previous embodiments 1, wherein the long chain fatty acid ester comprises at least one fatty acid ester in which $R^1$ is an unsaturated hydrocarbon.

EMBODIMENT 6

The composition of any of the previous embodiments, wherein the long chain fatty acid ester comprises at least one fatty acid ester in which $R^1$ is an unsaturated hydrocarbon.

EMBODIMENT 7

The composition of any of the previous embodiments, wherein the long chain fatty acid ester comprises a plant-derived fatty acid ester group derived from at least one of linoleic acid, linolenic acid, oleic acid, stearic acid, and esters thereof.

EMBODIMENT 8

The composition of any of the previous embodiments, wherein the short chain fatty acid ester comprises at least one fatty acid ester group $R^2(O)O$—, wherein $R^2$ is a $C_8$-$C_{10}$ hydrocarbon.

EMBODIMENT 9

The composition of any of the previous embodiments, wherein the short chain fatty acid ester comprises at least one plant based fatty acid ester derived from capric and caprylic acids or esters thereof.

EMBODIMENT 10

The composition of any of the previous embodiments, wherein the short chain fatty acid ester comprises at least one of hexanoate, heptanoate, caprylate, pelargonate, and caprate, of methyl glucoside, and combinations thereof, and the long chain glucoside ester comprises at least one of laurate, myristate palmitate, stearate, isostearate, linoleate, linolenate, oleate, and behenate of methyl glucoside, and combinations thereof.

EMBODIMENT 11

The composition of any of the previous embodiments, wherein the rheology modifier comprises alkyl glucoside esters derived from caprylic acid, capric acid, and plant-based oleic acid, or their esters.

EMBODIMENT 12

The composition of any of the previous embodiments, wherein a ratio of long chain fatty acid ester groups to short chain fatty acid ester groups in the rheology modifier is at least 0.1:1.

EMBODIMENT 13

The composition of any of the previous embodiments, wherein the ratio of long chain fatty acid ester groups to short chain fatty acid ester groups in the rheology modifier is at least 0.2:1.

EMBODIMENT 14

The composition of any of the previous embodiments, wherein the ratio of long chain fatty acid ester groups to short chain fatty acid ester groups in the rheology modifier is at least 0.3:1.

EMBODIMENT 15

The composition of any of the previous embodiments, wherein a molar ratio of long chain fatty acid ester groups to short chain fatty acid ester groups in the rheology modifier is less than 1:1.

EMBODIMENT 16

The composition of any of the previous embodiments, wherein the ratio of long chain fatty acid ester groups to short chain fatty acid ester groups in the rheology modifier is up to 0.8:1.

EMBODIMENT 17

The composition of any of the previous embodiments, wherein the molar ratio of long chain fatty acid ester to short chain fatty acid ester groups in the rheology modifier is up to 0.7:1.

EMBODIMENT 18

The composition of any of the previous embodiments, wherein a molar ratio of long chain fatty acid ester groups to short chain fatty acid ester groups in the rheology modifier is 0.2:1 to 0.8:1.

EMBODIMENT 19

The composition of any of the previous embodiments, wherein the long chain fatty acid ester comprises plant-based oleic ester groups and the short chain fatty acid ester comprises caprylic and capric ester groups and wherein a molar ratio of unsaturated C18 ester groups to other ester groups (O/CC ratio) is from 0.2:1 to 0.7:1.

EMBODIMENT 20

The composition of any of the previous embodiments, wherein the O/CC ratio is from 0.35:1 to 0.6:1.

EMBODIMENT 21

The composition of any of the previous embodiments, wherein a degree of esterification per molecule of glycoside is from 0.7:1 to 1.5:1.

EMBODIMENT 22

The composition of any of the previous embodiments, wherein the degree of esterification is from 0.8:1 to 1.2:1.

EMBODIMENT 23

The composition of any of the previous embodiments, wherein the alkyl glycoside comprises an alkyl glucoside.

EMBODIMENT 24

The composition of any of the previous embodiments, wherein the alkyl glucoside is a $C_1$-$C_{30}$ alkyl glucoside.

EMBODIMENT 25

The composition of any of the previous embodiments, wherein the alkyl glucoside comprises methyl glucoside.

EMBODIMENT 26

The composition of any of the previous embodiments, wherein the alkyl glycoside fatty acid esters have a molecular weight of less than 1000.

EMBODIMENT 27

The composition of any of the previous embodiments, further comprising a non-aqueous solvent.

EMBODIMENT 28

The composition of any of the previous embodiments, wherein the rheology modifier increased the viscosity of the composition by a factor of at least 10 when the alkyl glycoside fatty acid esters are at a total concentration of up to 4 wt. % of the surfactant composition, as compared to an otherwise identical composition without the rheology modifier.

EMBODIMENT 29

The composition of any of the previous embodiments, wherein none of the alkyl glycoside fatty acid esters in the rheology modifier is alkoxylated.

EMBODIMENT 30

The composition of any of the previous embodiments, wherein the rheology modifier is present at a concentration of at least 0.1 wt. %.

EMBODIMENT 31

The composition of any of the previous embodiments, wherein the rheology modifier is present at a concentration of at least 0.5 wt. %.

EMBODIMENT 32

The composition of any of the previous embodiments, wherein the rheology modifier is present at a concentration of at least 1 wt. %.

EMBODIMENT 33

The composition of any of the previous embodiments, wherein the rheology modifier is present at a concentration of up to 5 wt. %

EMBODIMENT 34

The composition of any of the previous embodiments, wherein the rheology modifier is present at a concentration of up to 3 wt. %.

EMBODIMENT 35

The composition of any of the previous embodiments, wherein the surfactant is present at a concentration of at least 0.01 wt. %.

EMBODIMENT 36

The composition of any of the previous embodiments, wherein the surfactant is present at a concentration of at least 1 wt. %.

EMBODIMENT 37

The composition of any of the previous embodiments, wherein the surfactant is present at a concentration of up to 20 wt. %.

EMBODIMENT 38

The composition of any of the previous embodiments, wherein a ratio by weight of the alkyl glycoside fatty acid esters to the surfactant is less than 1:1.

EMBODIMENT 39

The composition of any of the previous embodiments, wherein a ratio by weight of the alkyl glycoside fatty acid esters to the surfactant is up to 0.5:1.

EMBODIMENT 40

The composition of any of the previous embodiments, wherein the surfactant comprises an anionic surfactant.

EMBODIMENT 41

The composition of any of the previous embodiments, wherein the surfactant further comprises a zwitterionic surfactant.

EMBODIMENT 42

The composition of any of the previous embodiments, wherein the composition is free of alkoxylated surfactants.

EMBODIMENT 43

The composition of any of the previous embodiments, wherein the composition is free of sulfate based surfactants.

EMBODIMENT 44

The composition of any of the previous embodiments, wherein the rheology modifier is not alkoxylated.

EMBODIMENT 45

The composition of any of the previous embodiments, further comprising at least 0.1% of a salt selected from soluble inorganic salts and organic salts having a molecular weight of less than 300.

EMBODIMENT 46

The composition of any of the previous embodiments, wherein the salt comprises a soluble inorganic salt.

EMBODIMENT 47

The composition of any of the previous embodiments, wherein composition comprises at least 0.2% of the soluble inorganic salt.

EMBODIMENT 48

The composition of any of the previous embodiments, wherein the composition comprises at least 40 wt. % water.

EMBODIMENT 49

The composition of any of the previous embodiments, wherein the composition has a viscosity of at least 1000 mPa·s, when measured at 24 hours after formation of the composition.

EMBODIMENT 50

The composition of any of the previous embodiments, wherein the composition has a viscosity of at least 2000 mPa·s, measured at 20° C., 24 hours after formation of the composition.

EMBODIMENT 51

The composition of any of the previous embodiments, wherein the composition has a viscosity of up to 10,000 mPa·s, measured at 20° C., 24 hours after formation of the composition.

EMBODIMENT 52

The composition of any of the previous embodiments, wherein the composition has a turbidity of less than 60 NTU, measured at 24 hours after formation of the composition.

EMBODIMENT 53

The composition of any of the previous embodiments, wherein the composition has a turbidity of less than 30 NTU, at 24 hours after formation.

EMBODIMENT 54

The composition of any of the previous embodiments, wherein the composition is formed by mixing the surfactant and rheology modifier with water at ambient temperature.

EMBODIMENT 55

The composition of any of the previous embodiments, further comprising at least one of silicones, emollients, silicones, emulsifiers, pearlescent agents, coloring agents, particulates, preservatives, pH adjusting agents, botanicals, chelating agents, antimicrobials, and auxiliary rheology modifiers.

EMBODIMENT 56

The composition of any of the previous embodiments, wherein the composition is formulated for a personal care application selected from a shampoo, a body wash, a liquid soap, a facial cleanser, and a hand soap.

EMBODIMENT 57

A method of forming a composition comprising: combining a rheology modifier with an anionic surfactant and water, the rheology modifier comprising a mixture of alkyl glycoside fatty acid esters comprising:
a long chain fatty acid ester of an alkyl glycoside, the long chain fatty acid ester consists of at least one fatty acid ester group $R^1(O)O$—, wherein $R^1$ is a $C_{12}$ or higher hydrocarbon, and
a short chain fatty acid ester of an alkyl glycoside, the short chain fatty acid ester consisting of least one fatty acid ester group: $R^2(O)O$—, wherein $R^2$ is a $C_6$-$C_{10}$ hydrocarbon.

EMBODIMENT 58

The method of embodiment 57, wherein the combining is performed at ambient temperature.

EMBODIMENT 59

The method of embodiments of 57 and 58, further comprising forming the rheology modifier comprising: separately or in combination, reacting an alkyl glycoside with a long chain fatty acid of the formula $R^1(O)OH$ or derivative thereof and with a short chain fatty acid of the formula $R^2(O)OH$ or derivative thereof.

EMBODIMENT 60

A rheology modifier comprising a mixture of alkyl glycoside fatty acid esters comprising:
a long chain fatty acid ester of an alkyl glycoside, the long chain fatty acid ester consisting of at least one fatty acid ester group $R^1(O)O$—, wherein $R^1$ is a $C_{12}$-$C_{23}$ hydrocarbon group, and
a short chain fatty acid ester of an alkyl glycoside, the short chain fatty acid ester consisting of least one fatty acid ester group $R^2(O)O$—, wherein $R^2$ is a $C_6$-$C_{10}$ hydrocarbon group; and
wherein a ratio of $R^1(O)O$— to $R^2(O)O$— in the rheology modifier is from 0.2:1 to 0.7:1.

EMBODIMENT 61

The rheology modifier of embodiment 60, wherein $R^1$ comprises a mixture of $C_8$ and $C_{10}$ hydrocarbon groups derived from caprylic and capric acids or derivatives thereof and $R^2$ comprises a mixture of $C_{18}$ hydrocarbon groups derived from plant-based oleic acid or derivatives thereof.

EMBODIMENT 62

A composition comprising a rheology modifier derived from a reaction of an alkyl glycoside with a long chain fatty acid or derivative thereof and a short chain fatty acid or derivative thereof, the short and long chain fatty acids or derivatives thereof including a hydrocarbon chain of at least 6 carbons in length, and wherein the short and long chain fatty acids or derivatives thereof differ in the length of their respective hydrocarbon chains by an average of at least 6 carbon atoms.

EMBODIMENT 63

The composition of embodiment 62, further comprising a surfactant.

EMBODIMENT 64

The composition of any of embodiments 62 and 63, further comprising water.

EMBODIMENT 65

The composition of any of embodiments 62, 63 and 64, wherein a molar ratio of the long chain fatty acid or derivative thereof to the short chain fatty acid or derivative thereof is less than 1:1.

BRIEF DESCRIPTION OF THE DRAWING

FIG. 1 is a plot showing the viscosity of MeG-CCO (Example G) in 20% Zemea, using a DV-II+ Pro Brookfield viscometer and SPDL SC4-27, rotating at 20 rpm; at 20° C.

DETAILED DESCRIPTION

Embodiments disclosed herein relate to a rheology modifier and to aqueous surfactant-based compositions thickened with the rheology modifier. The exemplary rheology modifier disclosed herein is a mixture of short and long chain fatty acid esters of an alkyl glycoside.

The exemplary rheology modifier may find use in personal care products, such as personal care cleansing products, cosmetics, toiletries, beauty aids, insect repellents, personal hygiene products, household cleansing products, and the like. The rheology modifier finds particular use in liquid aqueous compositions containing surfactants that are useful in the formulation of personal care cleansing products intended to be applied to the body, including the skin, hair, scalp, and nails of humans and animals. Examples of such personal care cleansing products include shampoos, liquid soaps, body washes, facial cleansers (including facial rinses), and the like. However, the exemplary rheology modifier may also find application in other surface cleaning applications or in maintaining sanitary conditions the home, or in institutional and industrial environments, in textile treatments (e.g., textile conditioners, carpet and upholstery cleaners), automobile care (e.g., hand and automatic car wash detergents, tire shines, leather conditioners, liquid car polishes, plastic polishes and conditioners), paints and coatings, and the like.

Embodiments disclosed herein provide an efficient non-polymeric, rheology modifier, suitable for use in aqueous surfactant-based cleansing compositions, which can be free of alkylene oxide (e.g., ethylene oxide), e.g., polyethylene glycol (PEG)-free, and which can be made entirely from safe, renewable, vegetable derived starting materials, which are considered "green." By alkylene oxide free, it is meant that the aqueous surfactant-based cleansing composition includes less than 1 wt. % poly(alkylene oxide), such as no more than 0.1 wt. % or 0.01 wt. %. The fatty acid esters of alkyl glycosides such as methyl glucoside are compatible with a number of anionic, zwitterionic and nonionic surfactants as well as with electrolytes and a number of formulation adjuvants typically used in the preparation of aqueous surfactant compositions.

Without being bound by any particular theory, it is believed that the exemplary rheology modifiers disclosed herein increase the viscosity of aqueous surfactant compositions by association with the surfactant micelles and thus can be considered as associative thickeners or micellar thickeners.

The exemplary glycosides, such as methyl glucosides, have a high stability, as compared with unsubstituted sugars, when used in forming fatty acid esters. The rheology modifier has a high clarity, making it particularly useful in personal care products.

The Rheology Modifier

The exemplary rheology modifier includes fatty acid esters of a glycoside, which may be referred to herein as glycoside esters, one specific example of which are methyl glucoside esters, which are fatty acid esters of methyl glucoside (MeG). For ease of discussion, the rheology modifier can be considered to include a glycoside component, derived from a glycoside molecule or "core," and a fatty acid component, comprising one or more fatty acid groups linked to each glycoside molecule, the fatty acid groups comprising fatty acid groups derived from first and second fatty acids A and B, which differ in their chain lengths.

1. Glycoside Component

Exemplary glycosides for forming the rheology modifier comprise a sugar molecule (typically a monomer), which is bound to a non-carbohydrate moiety through the anomeric carbon, and in particular, via an oxygen linkage. Exemplary glycosides are glucosides (glycosides derived from glucose), although other glycosides are also contemplated, such as glycosides of other cyclic monosaccharides, particularly other cyclic hexoses such as galactosides and fructosides, more particularly, cyclic hexoses having a six-membered ring.

Exemplary non-carbohydrate moieties which may be bound to the sugar molecule by a covalent bond include alkyl groups. An alkyl glycoside generally refers to a glycoside in which the alkyl group is bonded via a glycosidic bond to the anomeric carbon. Exemplary alkyl groups include as linear and branched $C_1$-$C_{30}$ alkyls, in particular, $C_1$-$C_{10}$ alkyls, such as methyl, ethyl, propyl, butyl, pentyl (amyl), and mixtures thereof. Exemplary alkyl glycosides are short chain ($C_1$-$C_{10}$) alkyl glucosides, such as methyl glucoside, ethyl glucoside, propyl glucoside, butyl glucoside, and pentyl glucoside. While particular reference is made herein to alkyl glucosides, such as methyl glucoside (MeG), as the exemplary glycosides, it is to be appreciated that other glycosides are also contemplated.

An advantage of glycosides is that they tend to be hydrolytically and thermally stable polyols containing greater than 95 wt. % monosaccharide. However, it is to be appreciated that the polyol may include a larger proportion of polyols that include polysaccharides (disaccharides and higher). In general, a ratio of glycoside in the monosaccharide form to the polysaccharide form is at least 1:1, such as at least 5:1, or at least 10:1.

Suitable alkyl glucosides useful in forming the rheology modifier are represented in Structure 1:

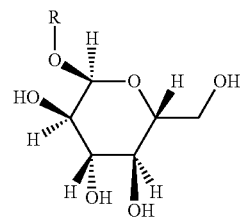

Structure 1 where
$R=C_nH_{2n+1}$ where n=1 to 30, such as 1-10 (e.g., —$CH_3$, —$C_2H_5$, —$C_3H_7$, or —$C_4H_9$).

Suitable R groups include linear and branched hydrocarbons that are naturally obtained, such as from vegetable sources. As will be appreciated, one or more of the hydroxyls (but not all) in Structure 1 can be replaced with hydrogen.

An exemplary glycoside is methyl glucoside (MeG), e.g., with a purity of at least 95 wt. % or at least 98 wt. %. Such a material can be obtained from Lubrizol Corp, Cleveland, Ohio, USA.

While structure 1 illustrates a monosaccharide, polysaccharides of from 1-10 glucose residues in length are also contemplated. The glucose residues in the polysaccharide may be linked via a 1,4-linkage.

Fatty Acid Component

Lipophilic compounds suitable for forming the ester of the glycoside through an esterification or trans-esterification reaction include compounds which are reactive with the glycoside and which have sufficient molecular weight to promote associative thickening when introduced into an aqueous, surfactant-containing system. Exemplary lipophilic compounds include fatty acids and fatty acid esters having from 6-23 carbon atoms in the hydrocarbon chain.

Examples of suitable fatty acids/esters include natural and synthetic saturated and unsaturated acids/esters which are linear or branched. The fatty acids or their esters can be used alone or as a mixture. Exemplary naturally derived fatty acids include saturated and unsaturated $C_6$-$C_{22}$ linear and branched fatty acids. Suitable linear fatty acids/esters include fatty acids and fatty acid esters of the general form shown in Structures 2 and 3:

$R^1(O)OR^3$     Structure 2

$R^2(O)OR^3$     Structure 3 where $R^1$ and $R^2$ each represents a linear or branched saturated or unsaturated aliphatic hydrocarbon chain, such as a $C_6$-$C_{23}$ chain or "tail," or a mixture thereof, where $R^2$ has fewer carbon atoms in the chain, on average, than $R^1$; and each $R^3$ represents H or an alkyl group, such as a $C_1$-$C_{10}$ alkyl group, e.g., methyl, ethyl, or propyl, butyl, or a mixture thereof. When reacted with the alkyl glycoside, these provide ester groups or fatty acid residues of the general form $R^1(O)O$— and $R^2(O)O$—.

Examples of suitable acids and esters, where the degree of unsaturation is listed after the number of carbons in the tail, include caproic acid (hexanoic acid, $R^1=C_6$: 0), enanthic acid (heptanoic acid, $R^1=C_7$: 0), caprylic acid (octanoic acid, $R^1=C_8$: 0), pelargonic acid (nonanoic acid, $R^1=C_9$: 0), capric acid (decanoic acid, $R^1=C_{10}$: 0), undecanoic acid ($R^1=C_{11}$: 0), lauric acid (dodecanoic acid, $R^1=C_{12}$: 0), myristic acid (tetradecanoic acid, $R^1=C_{14}$: 0), palmitic acid (hexadecanoic acid, $R^1=C_{16}$: 0), stearic acid (octadecanoic acid, $R^1=C_{18}$: 0), isostearic acid ($C_{17}$-methylheptadecanoic acid, $R^1=C_{18}$:

0), linoleic acid (cis, cis-9,12-octadecadienoic acid, $R^1=C_{18}$: 2), linolenic acid (either or both of all-cis-9,12,15-octadecatrienoic acid and all-cis-6,9,12-octadecatrienoic acid, $R^1=C_{18}$: 3), oleic acid (cis-9-octadecenoic acid, $R^1=C_{18}$: 1), vaccenic acid ((E)-11-octadecenoic acid, $R^1=C_{18}$: 1), eicosanoic acid ($R^1=C_{20}$: 0), gadoleic acid (cis-icos-9-enoic acid, $R^1=C_{20}$: 1), arachidonic acid (5Z,8Z,11Z,14Z)-5,8,11, 14-eicosatetraenoic acid, $R^1=C_{20}$: 4), eicosapentaenoic acid (5Z,8Z,11Z,14Z,17Z)-5,8,11,14,17-icosapentaenoic acid, $R^1=C_{20}$: 5), heneicosanoic acid ($R^1=C_{21}$: 0), behenic acid (docosanoic acid, $R^1=C_{22}$: 0), erucic acid ((Z)-docos-13-enoic acid $R^1=C_{22}$: 1), lignoceric acid (tetracosanoic acid $R^1=C_{23}$: 0), and esters, and mixtures thereof. For example, alkyl esters having 1 to 8 carbon atoms such as a methyl, ethyl or propyl ester of the fatty acid described above can be used. These acids are all non-hydroxylated. In some embodiments, hydroxylated acids, such as ricinoleic acid (12-hydroxy-9-cis-octadecenoic acid), may be employed.

The exemplary acids can be plant-based, e.g., obtained from vegetable oils such as coconuts oils, palm oil, linseed oil, soybean oil, sunflower oil, and the like. Commercially available acids derived from plants may contain mixtures of two or more acids.

A suitable long chain fatty acid is a plant-based fatty acid sold as "oleic acid" and is actually a mixture of fatty acids of Structure 2, where $R^1=C_{13}$ to $C_{22}$, with an average carbon chain length of approximately 16-18, and which is predominantly a mixture of oleic, linolenic, linoleic, and stearic acids. Accordingly, where reference is made herein to plant-based oleic acid (or its ester), it means a mixture which is predominantly (greater than 60 wt. %, or greater than 70 wt. %, or greater than 80 wt. %) unsaturated $C_{18}$ carboxylic acids, together with other acids in smaller amounts.

Another long chain plant-based fatty acid, sold as "myristic acid," is actually a mixture of acids of Structure 2, where $R^1=C_{13}$ to $C_{16}$, with an average carbon chain length of approximately 14, and which is predominantly $R^1=C_{14}$.

A suitable short chain plant-based fatty acid (or ester), sold as "capric/caprylic acid," is actually a mixture of fatty acids of Structure 3, where $R^3=C_6$ to $C_{10}$, and which is predominantly (greater than 60 wt. %, or greater than 70 wt. %, or greater than 80 wt. %) $R^3=C_8+C_{10}$. A ratio of $C_8:C_{10}$ in the plant-based capric/caprylic acid/ester may be, for example, from 1:2 to 3:1 such as from 1.5:1 to 1:1.1, or about 1.2:1.

As will be appreciated, when plant derived, the material used as the long chain plant-based fatty acid/ester may contain minor amounts of $C_{11}$ and lower fatty acids/ester of Structure 3, such as up to 2 wt. %, or up to 1 wt. %, or up to 0.1 wt. %. Typically the $C_{11}$ and lower fatty acid/ester content of the mixture is predominantly $C_{10}$. Also, when plant derived, the material used as the short chain plant-based fatty acid/ester may contain minor amounts of $C_{11}$ and higher fatty acids/ester of Structure 2, such as up to 2 wt. %, or up to 1 wt. %. Typically the $C_{11}$ and higher fatty acid/ester content of the mixture is predominantly $C_{12}$. However, for purposes of weight ratios and so forth discussed herein, $R^1$ and $R^2$ include only the specified hydrocarbons.

In forming the exemplary esterified alkyl glycosides, the exemplary alkyl glycosides can be mono, di, tri, or tetra substituted with the acid/ester. For example, esterified alkyl glucosides may have the formula shown in Structure 4:

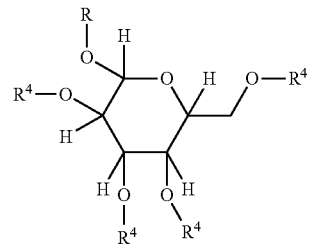

Structure 4 where each $R^4$ is independently $R^1(O)—$, $R^2(O)—$, or H, and where $R^1$ and $R^2$ are as defined above and at least one of $R^4$ is not H. In the radicals, $R^1(O)—$ and $R^2(O)—$, as used here and throughout the specification each $R^1$ and $R^2$ taken together with the carbonyl oxygen atom, (O), represent an acyl group. In other words, a terminal carbon atom in each of hydrocarbon groups $R^1$ and $R^2$ are carbonyl carbons.

The exemplary lipophilic component can thus be a green or naturally derived hydrocarbon or substituted hydrocarbon moiety having 6 to 23 carbon atoms per molecule which is covalently bonded to the glycoside core.

In the exemplary embodiment, the esterified glycoside is formed using a mixture of esters/acids wherein the mixture includes:

a) at least one fatty acid or fatty acid ester A of Structure 2 wherein $R^1$ is a branched or unbranched $C_{12}$ or higher hydrocarbon, e.g., a $C_{12}$-$C_{23}$ hydrocarbon, such as at least one of lauric acid, myristic acid, palmitic acid, stearic acid, isostearic acid, linoleic acid, linolenic acid, oleic acid, and behenic acid, or ester thereof.

b) at least one fatty acid or fatty acid ester B of Structure 3 wherein $R^2$ is a branched or unbranched $C_{10}$ or lower aliphatic hydrocarbon, e.g., a $C_6$-$C_{10}$ hydrocarbon, such as at least one of caproic acid, enanthic acid, caprylic acid, pelargonic acid, and capric acid, or ester thereof.

In one embodiment, in the fatty acid or fatty acid ester of Structure 2, $R^1$ includes a $C_{12}$-$C_{23}$ aliphatic hydrocarbon, or mixture thereof. For example, the fatty acid ester used in preparing esterified glycoside may be at least 50 wt. %, or at least 70 wt. %, or at least 90 wt. % of the compounds of Structure 2 and wherein $R^1$ is a $C_{12}$-$C_{23}$ aliphatic hydrocarbon, or a $C_{13}$-$C_{21}$ hydrocarbon.

In one embodiment, in the fatty acid or fatty acid ester of Structure 3, $R^2$ includes a $C_6$-$C_{10}$ aliphatic hydrocarbon, or mixture thereof. For example, the fatty acid ester used in preparing esterified glycoside may be at least 50 wt. %, or at least 70 wt. %, or at least 90 wt. % of the compounds of Structure 3 and wherein $R^2$ is a $C_6$-$C_{10}$ aliphatic hydrocarbon, or is predominantly (e.g., at least 80 wt. %, or at least 90 wt. %, or at least 95 wt. % and up to 100 wt. %) a $C_8$-$C_{10}$ aliphatic hydrocarbon.

In one embodiment, the long chain fatty acid or derivative thereof and short chain fatty acid or derivative thereof differ in their average hydrocarbon chain number of carbon atoms by at least 4 or at least 6, or at least 8.

In general, the rheology modifier includes more substituent groups derived from the short chain fatty acid/ester B than from the long chain fatty acid/ester A. For example, a molar ratio of long chain fatty acid or fatty acid ester of Structure 2: short chain fatty acid or fatty acid ester of Structure 3 used in preparing the esterified alkyl glycoside (and/or the corresponding ester groups in the esterified alkyl glycoside formed), may be from 0.1:1 to 1:1, such as at least 0.2:1, or at least 0.3:1, and may be up to 0.9:1, or up to 0.9:1, or up to 0.7:1.

A degree of esterification, which is the average number of $R^3$ groups (other than H) per alkyl glycoside molecule, e.g., the molar equivalents of fatty acid groups to methyl glucoside, can be from 0.7:1 to 1.5:1, such as up to 1.3:1, e.g., from 0.8:1 to 1.2:1, or from 0.9:1 to 1.1:1, i.e., about 1:1. In one embodiment, the degree of esterification is at least 0.9:1.

By balancing the degree of esterification as well as the ratio of fatty acid groups of Structure 2 to those of Structure 3 (A:B ratio), a suitable thickener for surfactant compositions is obtained which provides an unexpectedly high viscosity per mole or unit weight of the esterified alkyl glycoside.

Exemplary non-limiting examples of rheology modifiers include mixtures of glucoside esters including:

a) a long chain glucoside ester including at least one ester group selected from laurate, myristate palmitate, stearate, isostearate, linoleate, linolenate, oleate, and behenate, and combinations thereof; and b) a short chain glucoside ester including at least one at least one ester group selected from hexanoate, enanthate, caprylate (octanoate), decanoate, pelargonate acid, and undecanoate, and combinations thereof.

In specific examples, the long chain glucoside ester includes glucoside oleate or a mixture of esters derived from natural (plant-based) oleic acid ($C_{13}$-$C_{22}$ acids).

In specific examples, the long chain glucoside ester includes an unsaturated alkylate group.

In specific examples, the short chain glucoside ester includes alkyl glucoside octanoate and alkyl glucoside decanoate, such as methyl glucoside octanoate and methyl glucoside decanoate, which may be derived from a mixture of capric and caprylic acids, or may be at least one of these.

In specific examples, none of the fatty acid esters of methyl glucoside constituting the rheology modifier is alkoxylated.

As will be appreciated, when the rheology modifier is formed in a single reaction where each of the fatty acid groups is present, the resulting rheology modifier may include glucoside cores which are each mono-, di-, tri-, or tetra-substituted with any one or more of the fatty acid groups present in the reaction.

The resulting rheology modifier may be considered as consisting of the reaction product of the selected glycoside(s) with the selected short and long chain fatty acids and/or ester thereof, ignoring any solvent as well as water or alcohol produced as a byproduct of the reaction (which can be removed), but including any unreacted glycoside and fatty acid or ester, if any.

By way of example, one exemplary rheology modifier is an ester mixture of methyl glucoside esters of plant-based caprylic/capric acids and plant-based oleic acid. This mixture of methyl glucoside esters is referred to herein as MeG-CCO. The ratio of unsaturated alkyl ester groups (predominantly $C_{18}$) to other alkyl ester groups of methyl glucoside (predominantly short chain $C_8$+$C_{10}$) in the rheology modifier is referred to herein as the O/CC ratio. In the ratios specified herein, the O/CC ratio is as determined by NMR. However, it will be appreciated that it generally corresponds to the ratio the moles of each of the components used in forming the rheology modifier. More generally, the O/CC ratio closely corresponds to the A:B ratio, where A represents the equivalent moles of alkyl ester groups derived from an acid or derivative thereof according to Structure 2 in the rheology modifier and B represents the equivalent moles of alkyl ester groups derived from an acid or derivative thereof according to Structure 3 in the rheology modifier. The O/CC (or A:B) ratio can be in the range of 0.1:1 to 0.9:1, or 0.2:1 to 0.7:1, or 0.35:1 to 0.6:1, although other ratios are contemplated. The rheology modifier can be readily formed by the trans-esterification reaction of methyl glucoside with a mixture of short and long carbon chain esters, such as methyl esters, of plant-based caprylic, capric and oleic acids.

Another exemplary rheology modifier is an ester mixture of methyl glucoside esters of caprylic, capric and lauric acids. This mixture of methyl glucoside esters is referred to herein as MeG-CCL. The A:B ratio can be in the range of 0.35:1 to 0.8:1, such as at least 0.5:1, although other ratios are contemplated.

Chemical Synthesis of Glycoside Fatty Acid Esters

The exemplary fatty acid esters (e.g., MeG-alkyl and alkenyl esters, which may all referred to herein as MeG-alkyl esters for convenience) can be prepared by reacting an alkyl glycoside with a lipophilic esterifying or trans-esterifying reagent, such as a fatty acid or ester thereof. The reaction can be carried out under conditions such that a desired degree of esterification is achieved. Additionally, or alternatively, the ratio of fatty acid esterifying substituents: alkyl glycoside can be selected in such way to optimize, e.g., approximately maximize, the viscosifying properties and efficiency of the thickener.

The fatty acid esters of the alkyl glycoside can be synthesized by various methods, including ester synthesis using conventional catalysts or enzyme, such as lipase, and the like.

The rheology modifier may be derived from a reaction of an alkyl glycoside with a long chain fatty acid or derivative thereof and a short chain fatty acid or derivative thereof which differ in their hydrocarbon chain length by, for example, at least 4 at least 6 carbon atoms, on average.

Exemplary methods of synthesis include (1) an ester exchange reaction between starting oils or fats and alkyl glycoside; (2) an ester exchange reaction between a lower alkyl ester of a fatty acid and alkyl glycoside; (3) an ester synthesis between a fatty acid and alkyl glycoside; (4) a synthesis using a fatty acid chloride and alkyl glycoside. Since process (4) yields acyl chlorides, this process is generally unsuited to forming personal care formulations.

By way of example, methyl glucoside fatty esters may be obtained by reaction of methyl glucoside (MeG) with esterifying or trans-esterifying agents. The esterifying or trans-esterifying reagents are fatty acids or fatty acid esters which can be obtained from vegetable oils. The reagents provide an ester linkage to the polyol according to the following simplified reaction scheme shown in Scheme 1:

Scheme 1

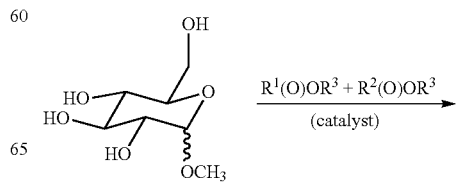

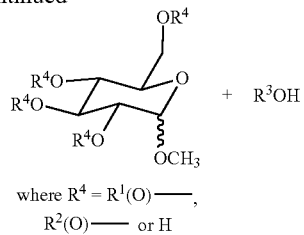

where $R^4 = R^1(O)\text{---}$, $R^2(O)\text{---}$ or H

The reaction in Scheme 1 above shows the trans-esterification reaction of methyl glucoside (MeG) with fatty acid alkyl esters, where $R^1$, $R^2$ and $R^3$ are as defined above. It is to be appreciated that at least one of $R^4$ is $R^1(O)$— or $R^2(O)$—, i.e., at least a mono ester, however, it should be noted that depending on the stoichiometric ratio of reagents, various kinds of mono-, di-, tri- and tetra-esters can be formed. Furthermore, while two fatty acid alkyl esters are shown, more than two can be used in the reaction to generate the mixed polyesters with various degrees of esterification.

Heat and catalysts may be provided to effect the reaction, as well as suitable conditions to remove methanol (in the case of trans-esterification with an ester) or water (in the case of direct esterification with an acid) which are the typical byproducts of these reactions.

The esterification and transesterification reactions may be conducted under atmospheric or sub-atmospheric pressure, e.g., from 0.001 to 1.5 atmospheres (about 0.1 to 150 kPa), e.g., about 1 atm (about 100 kPa), and at a temperature in the range of 110° C. to 180° C. Catalysts may be employed to enhance the reaction rate. The catalysts can be acidic, basic, or neutral. Exemplary catalysts for the reaction include alkali metals and hydroxides and salts thereof, such as Na, $NaOCH_3$, $KOCH_3$, NaOH, KOH, $Na_2CO_3$, $K_2CO_3$; acids including p-toluenesulfonic acid ("p-TSA"), $H_2SO_4$, HCl, organic titanates, e.g., tetraisopropyl titanate. Sodium carbonate is used by way of example. In some cases, no catalyst is needed for the reaction to proceed at an acceptable rate.

As will be appreciated, this reaction scheme can be adapted to any of the short and long chain esters/acids represented in Structures 2 and 3 above.

The exemplary method includes reaction of the glycoside, e.g., methyl glucoside with a mixture of short and long chain esters/acids. This can be achieved in a single synthesis reaction, where short and long chain fatty acids/esters $R^1(O)OR^3$ and $R^2(O)OR^3$ are used together. Alternatively, separate reactions may be employed, where the long chain and short chain esters/acids are separately reacted with a glycoside, which can be the same or different, and the reaction products combined. In the single synthesis process, some of the glucose cores may be substituted with both short chain and long chain acids/ester substituents, while in the separate reaction method, each glucose core is substituted with either long or short esters/acid substituent(s), but not both.

The rheology modifier that is the product of the esterification reaction may be in the form of a viscous, translucent paste. Although the paste product is suitable for packaging and formulation, it may be dissolved/dispersed in a suitable solvent to provide a pourable liquid thickener, which is more suitable for preparing viscous surfactant-containing liquid compositions, especially at room temperature. Any liquid capable of dissolving/dispersing the exemplary glycoside esters is suitable for use in forming a low viscosity, rheology modifier-based formulation. Exemplary diluent liquids of this type include water, glycols, and other solvents, particularly those that are plant derived, and which are considered safe and suitable for use in contact with human tissue, such as skin and eyes. Alkylene glycols having about 2 to 5 carbon atoms per molecule, such as ethylene glycol, 1,2-propanediol, 1,3-propanediol, 1,2-butanediol, 1,3-butanediol, 1,4-butanediol, and mixtures thereof are suitable glycols. Some glycols that are derived from vegetable sources, such as 1,2-propanediol, are selected when a high content of plant derived materials is desired in the final formulation. One such 1,2-propanediol is derived from corn and is available under the trade name Zemea® from E. I. du Pont de Nemours and Company, Delaware, USA.

When a diluent is used, the concentration of diluent in the rheology modifier-based formulation may be at least 10 wt. %, e.g., in the range of from 60 wt. % to 90 wt. %. The viscosity of the rheology modifier-based formulation can thus be adjusted to less than about 10,000 mPa·s, as measured with a DV-II+ Pro Brookfield viscometer and SPDL SC4-27, rotating at 20 rpm; at 20° C.

For example, FIG. 1 shows the variation in solution viscosity with temperature of a rheology-modifier-based formulation including MeG-CCO (MeG ester of caprate, caprilate and plant-based "oleate," as described above) and 20 wt. % 1,2-propanediol (Zemea®).

Aqueous Surfactant-Based Compositions

An exemplary aqueous surfactant-based composition includes at least one surfactant, a rheology modifier as described herein, and water. The composition may further include an organic solvent. A water-soluble salt, such as an inorganic salt, may also be present in the composition. Other additives may also be present, as described below. The composition is generally a liquid, although gels and solid and semisolid compositions are also contemplated.

The rheology modifier, as defined above (excluding diluents such as water and/or glycols), may be present in the aqueous surfactant-based composition at a concentration of at least 0.01 wt. %, such as at least 0.1 wt. %, or at least 0.2 wt. %, or at least 0.5 wt. %, or at least 1 wt. %. The rheology modifier may be present in the aqueous surfactant-based composition at a concentration of up to 10 wt. %, such as up to 5 wt. %, or up to 4 wt. %, or up to 3 wt. %, or up to 2 wt. %.

In one embodiment, the aqueous surfactant-based composition includes at least 40 wt. % water (e.g., deionized, distilled or purified), or at least 60 wt. % water, and can be up to 80 wt. %, or up to 90 wt. % or up to 98 wt. % water.

The surfactant(s) may be present in the aqueous surfactant-based composition at a total concentration of at least 0.001 wt. %, such as at least 0.01 wt. %, or at least 1 wt. % and can be present at up to 80 wt. %, or higher, depending on a desired application. In one aspect, the surfactant is present at a total concentration of at least 2 wt. % or at least 5 wt. %, or at least 6 wt. %, or at least 8 wt. %. In some aspects, the surfactant is present at a total concentration of up to 65 wt. %, or up to 30 wt. %, or up to 20 wt. %, or up to 18 wt. %, based upon the total weight of the aqueous surfactant-based composition. All surfactant concentrations herein are based on weight of the active component in the surfactant, even if used in diluted form.

In one embodiment, a ratio by weight of the exemplary rheology modifier (specifically, the alkyl glycoside fatty acid esters) to total surfactant is less than 1:1, such as up to 0.5:1, or up to 0.3:1, or up to 0.2:1, and in some embodiments, is at least 0.01:1, such as at least 0.1:1.

The aqueous surfactant-based composition may include one or more inorganic salts, such as sodium, potassium and ammonium halides, carboxylates, and citrate, e.g., sodium chloride. Organic salts of low molecular weight (<300) such as sodium benzoate, may also be used. The salt may be present in the aqueous surfactant-based composition at a concentration of at least 0.01 wt. %, such as at least 0.1 wt. %, or at least 0.2 wt. %, or at least 0.5 wt. %, and in some embodiments, may be present at up to 3 wt. %, such as up to 2 wt. %, e.g., about 1 wt. %, or less.

The clarity (turbidity) of a surfactant-based composition can be determined in Nephelometric Turbidity Units (NTU) employing a nephelometric turbidity meter (e.g., a Micro100 or Micro1000 Turbidimeter, available from HF Scientific, Inc.) at ambient room temperature of about 20 to 25° C. It is to be assumed that measurements are made at 20° C. by the following method, unless otherwise noted. Distilled water (NTU=0) is utilized as a standard. 25 ml screw cap vials (70 mm×25 mm) are filled almost to the top with test sample and warmed up to 55° C. for one hour until all bubbles are removed. Each sample vial is wiped with tissue paper to remove any smudges before placement in a turbidity meter. The sample is placed in the turbidity meter and a reading is taken. Once the reading stabilizes the NTU value is recorded. The vial is given one-quarter turn and another reading is taken and recorded. This is repeated until four readings are taken. The lowest of the four readings is reported as the turbidity value. Compositions having an NTU value of about 60 or greater are judged hazy or turbid. Compositions having an NTU value of less than about 30 are considered very clear. For samples having turbidity greater than 100 NTU, the Micro 1000 turbidimeter was used. Otherwise, the Micro 100 turbidimeter was used.

Exemplary aqueous surfactant-based compositions which include the exemplary rheology modifier can have an NTU value, determined by this method, of 60 or less, e.g., 50 or less, or 40 or less and in some embodiments, 30 or less, or 20 or less, even at concentrations of the rheology modifier at up to 4 wt. % of the composition.

Alkyl glycoside esters, and in particular, MeG ester mixtures which have been esterified with a mixture of relatively long and short carbon chain fatty acids, as disclosed herein, are capable of modifying the viscosity of a variety of aqueous surfactant-based compositions, such as cleansing compositions. For example, the viscosity of the exemplary aqueous surfactant based compositions formulated with the rheology modifiers disclosed herein may have a viscosity of at least 500 mPa·s (as measured with a DV-II+ Pro Brookfield viscometer and spindle SC421/13R, rotating at 20 rpm; at 20° C.±1° C., according to Brookfield Engineering Manual M/98-161-I496). In one aspect, the viscosity of the aqueous surfactant-based composition is at least 2000 mPa·s, or at least 3000 mPa·s, or at least 10,000 mPa·s, or at least 15,000 mPa·s, or at least 20,000 mPa·s, or a least 25,000 mPa·s by this method, and in some embodiments can be up to 30,000, 40,000, 50,000, or even 60,000 mPa·s or above. In one aspect, these viscosities are achieved when the rheological modifier itself is present at a concentration of no more than 5 wt. %, such as up to 4 wt. %, or up to 3 wt. %, or up to 2 wt. % of the aqueous surfactant-based composition.

In achieving these viscosities, the rheology modifier may increase the viscosity of the base aqueous surfactant-based composition (i.e., without the rheology modifier) by a factor of at least 2, such as at least 10, or at least 20. For example, an aqueous surfactant-based composition can have its viscosity increased from under 1000 mPa·s (or under 100 mPa·s) to at least 2000 mPa·s, when the rheology modifier is added at a concentration of no more than 5 wt. %, such as up to 4 wt. %, or up to 3 wt. %, or up 2 wt. %.

By way of example, experimental tests show that when the rheology modifier includes MeG-esters formed according to the methods disclosed herein, when added at a concentration from 0.5 wt. % to 4 wt. %, raised the viscosity of a base aqueous surfactant-based composition from about 20 mPa·s to greater than 60,000 mPa·s, depending on the surfactant composition. Cleansing formulations, which desirably have viscosity between 3,000 mPa·s and 10,000 mPa·s and turbidity of less than 30 NTU, are conveniently prepared by adjusting the concentration of the MeG-esters, e.g., to within the range of 0.01-2 wt. %, to achieve a desired viscosity.

In one aspect, the rheology modifier can achieve these viscosities despite a very low molecular weight. For example, the rheology modifier may have a number average molecular weight ($M_n$) of less than 1000 daltons, or up to 500 daltons.

The exemplary aqueous surfactant-based compositions can be prepared at room temperature (cold process). By room temperature, it is meant a temperature in the range of 15-40° C., such as under 30° C. The compositions may also be formed at higher temperatures, such as 40-70° C. However, there are advantages to a room temperature process, one of which being that it does not require the use of heat, saving energy and providing a concomitant benefit to the environment.

By way of example, when the rheology modifier is MeG-CCO (as noted above, a mixture of methyl glucoside esters of caprylic, capric and plant-based oleic acids), and the O/CC ratio (ratio of long (plant-based oleic) to short (capric/caprylic) esters of methyl glucoside) is in the range of 0.35 to 0.6, some or all of the following properties can be achieved:

1. A viscosity of greater than 2,000 mPa·s, even when the rheology modifier is used at less than 2.0 wt. % in a surfactant composition.

2. A high clarity, e.g., turbidity (NTU) of less than 60, or less than 50, or less than 30.

3. A long term shelf life stability.

4. A cold processing preparation of the surfactant composition.

5. A formulation which is synergistically compatible with salt and other formulation adjuvants.

6. A salt tolerant formulation.

7. A non-alkoxylated formulation.

Since MeG-CCO is nonionic in nature, it is not negatively affected by the presence of salt in the formulations as is the case with most charged polymeric thickeners. Furthermore, salts, such as sodium chloride and other salts, tend to work synergistically with MeG-CCO.

Additionally, MeG-CCO is a non-alkoxylated (PEG-free), hydrophobic, water insoluble, compound which easily disperses in water and in surfactant compositions at room temperature. In spite of its lack of solubility in water, MeG-CCO is able to form viscous, water-clear surfactant compositions, having turbidity of less than 30 NTU. This is unexpected since most conventional thickeners for cleansing formulations are hydrophilic, charged or ethoxylated, and very water soluble.

Furthermore, MeG-CCO, is non-alkoxylated, renewable, "green" or naturally derived compound which can be made from a stabilized glucose such as methyl glucoside, and various plant derived fatty acid esters. As such its non-animal, non-petroleum derived content of the rheology modifier can exceed 98 wt. %.

The exemplary MeG-esters, when added to the exemplary base aqueous surfactant-based compositions, can provide formulations which are mild and non-irritating to the skin or eyes. In some cases, they are also capable of reducing the irritation effect of the primary surfactants. As such, MeG-CCO and other MeG-ester mixtures can be used to prepare washing compositions amenable for human and animal subjects including infants having delicate or sensitive skin and eyes.

While the exemplary rheology modifier may function as a micellar thickener, other thickening mechanisms are also contemplated. Further information regarding the physical and chemical mechanisms through which the different kinds of thickeners confer viscosity to aqueous surfactant compositions is described, for example, in E. Desmond Goddard; "Principles of Polymer Science and Technology in Cosmetics and Personal Care" (Cosmetic Science and Technology), Publisher: Informa HealthCare; 1 edition (Mar. 10, 1999); J. E. Glass, "Polymers in Aqueous Media—Performance through Association".

The exemplary rheology modifier can be incorporated into a liquid cleansing or other surfactant-based composition by pouring and mixing the rheology modifier into the surfactant system at room temperature (cold process) or with gentle heating (hot process), as desired. The rheology modifier can be added at any step of the mixing process. This ease of mixing is an advantage over a number of conventional surfactant thickeners which require neutralization, heating or other costly and time consuming steps.

Exemplary Surfactants

Exemplary surfactants suitable for use in the surfactant-based compositions disclosed herein include anionic, zwitterionic (amphoteric), cationic, and nonionic surfactants, and mixtures thereof and may be present at from 0.1 wt. % to 40 wt. % of the surfactant-based composition. In one embodiment, the composition includes at least one anionic surfactant. The anionic surfactant(s) may be present in the aqueous surfactant-based composition at a total concentration of at least 0.001 wt. %, such as at least 0.1 wt. %, or at least 1 wt. %, or at least 5 wt. %. In one embodiment, the surfactant further includes a zwitterionic surfactant. The zwitterionic surfactant(s) may be present in the aqueous surfactant-based composition at a total concentration of at least 0.001 wt. %, such as at least 0.1 wt. %, or at least 1 wt. %, or at least 5 wt. %.

Anionic Surfactants

Suitable anionic surfactants for use in the aqueous surfactant-based composition include alkyl sulfates, alkyl ether sulfates, alkyl sulphonates, alkaryl sulfonates, α-olefin-sulphonates, alkylamide sulphonates, alkarylpolyether sulfates, alkylamidoether sulfates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof. Anionic surfactants having a high content of plant-derived mass are particularly suitable and include plant derived surfactants with a low content of petroleum-derived or alkoxylated surfactants.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants may contain from 6 to 24 carbon atoms in one aspect, from 8 to 22 carbon atoms in another aspect and from 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcosinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from 8 to 22 carbon atoms.

Cationic Surfactants

Cationic surfactants useful in the exemplary surfactant-based formulation can include any of the cationic surfactants known or previously used in the art of aqueous surfactant compositions. Suitable classes of cationic surfactants include alkyl amines, alkyl imidazolines, ethoxylated amines, quaternary compounds, and quaternized esters. Cationic surfactants particularly suitable for preparing the surfactant-based compositions have a high content of plant-derived mass, as noted above.

Alkylamine surfactants can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Examples of amidoamines and salts thereof include stearamidopropyl dimethylamine, stearamidopropyl dimethylamine citrate, palmitamidopropyl diethylamine, and cocamidopropyl dimethylamine lactate.

Examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Examples of ethyoxylated amines include PEG-cocopolyamine, PEG-15 tallow amine, quaternium-52, and the like.

Among the quaternary ammonium compounds useful as cationic surfactants, some correspond to the general formula: $(R^5R^6R^7R^8N^+)$ $E^-$, wherein $R^5$, $R^6$, $R^7$, and $R^8$ are independently selected from an aliphatic group having from 1 to 22 carbon atoms, or an aromatic, alkoxy, polyoxyalkylene, alkylamido, hydroxyalkyl, aryl or alkylaryl group having 1 to 22 carbon atoms in the alkyl chain; and E is a salt-forming anion such as those selected from halogen, (e.g., chloride, bromide), acetate, citrate, lactate, glycolate, phosphate, nitrate, sulfate, sulfonate, and alkylsulfate. The aliphatic groups can contain, in addition to carbon and hydrogen atoms, ether linkages, ester linkages, and other groups such as amino groups. The longer chain aliphatic groups, e.g., those of 12 carbons, or higher, can be saturated or unsaturated. In one aspect, the aryl groups are selected from phenyl and benzyl.

Exemplary quaternary ammonium surfactants may include cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl ammonium chloride, dihexadecyl dimethyl ammonium acetate, behenyl trimethyl ammonium chloride, benzalkonium chloride, benzethonium chloride, and di(coconutalkyl)dimethyl ammonium chloride, ditallowdimethyl ammonium chloride, di(hydrogenated tallow)dimethyl ammonium chloride, di(hydrogenated tallow)dimethyl ammonium acetate, ditallowdimethyl ammonium methyl sulfate, ditallow dipropyl ammonium phosphate, and ditallow dimethyl ammonium nitrate.

At low pH, amine oxides can protonate and behave similarly to N-alkyl amines. Examples include dimethyldodecylamine oxide, oleyldi(2-hydroxyethyl)amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

Zwitterionic Surfactants

Zwitterionic (or amphoteric) surfactants are molecules that contain acidic and basic moieties and have the capacity of behaving either as an acid or a base. Suitable surfactants can be any of the amphoteric surfactants known or previously used in the art of aqueous surfactant compositions. Exemplary amphoteric surfactant classes include amino acids (e.g., N-alkyl amino acids and N-acyl amino acids), betaines, sultaines, and alkyl amphocarboxylates. Particularly suitable zwitterionic surfactants are those having a high content of plant-derived mass, as noted above.

Amino acid based surfactants suitable for use in the exemplary surfactant-based composition include surfactants represented by the formula:

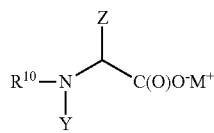

wherein $R^{10}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —$CH_2C_6H_4OH$, —$CH_2OH$, —$CH(OH)CH_3$, —$(CH_2)_4NH_2$, —$(CH_2)_3NHC(NH)NH_2$, —$CH_2C(O)O^-M^+$, —$(CH_2)_2 C(O)O^-M^+$. M is a salt forming cation. In one aspect, $R^{10}$ represents a radical selected from a linear or branched $C_{10}$ to $C_{22}$ alkyl group, a linear or branched $C_{10}$ to $C_{22}$ alkenyl group, an acyl group represented by $R^{11}C(O)$—, wherein $R^{11}$ is selected from a linear or branched $C_9$ to $C_{22}$ alkyl group, a linear or branched $C_9$ to $C_{22}$ alkenyl group. In one aspect, $M^+$ is selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants include the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

Betaines and sultaines useful herein may be selected from alkyl betaines, alkylamino betaines, and alkylamido betaines, as well as the corresponding sulfobetaines (sultaines) represented by the formulas:

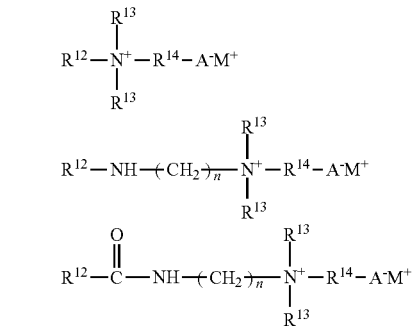

wherein $R^{12}$ is a $C_7$-$C_{22}$ alkyl or alkenyl group, each $R^{13}$ independently is a $C_1$-$C_4$ alkyl group, $R^{14}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{12}$ is a $C_{11}$-$C_{18}$ alkyl group or a $C_{11}$-$C_{18}$ alkenyl group. In one aspect, $R^{13}$ is methyl. In one aspect, $R^{14}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines may include lauryl betaine, cocamidopropyl betaine, coco betaine, oleamido propyl betaine, oleyl betaine, cocohexadecyl dimethylbetaine, lauryl amidopropyl betaine, and cocamidopropyl hydroxysultaine.

The alkylamphocarboxylates such as the alkylamphoacetates and alkylamphopropionates (mono- and disubstituted carboxylates) can be represented by the formula:

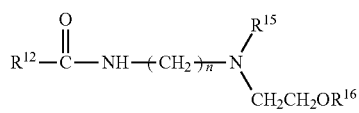

wherein $R^{12}$ is a $C_7$-$C_{22}$ alkyl or alkenyl group, $R^{15}$ is —$CH_2C(O)O^-M^+$, —$CH_2CH_2C(O)O^-M^+$, or —$CH_2CH(OH)CH_2SO_3^-M^+$, $R^{16}$ is a hydrogen or —$CH_2C(O)O^-M^+$, and M is a cation selected from sodium, potassium, magnesium, ammonium, and mono-, di- and triethanolamine.

Exemplary alkylamphocarboxylates may include sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Nonionic Surfactants

The nonionic surfactant can be any of the nonionic surfactants known or previously used in the art of aqueous surfactant compositions. Particularly suitable nonionic surfactants are those having a high content of plant-derived mass, as noted above. Suitable nonionic surfactants may include aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants may include alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glu-camate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357.

Other surfactants which can be utilized herein are set forth in more detail in WO 99/21530, U.S. Pat. No. 3,929,678, U.S. Pat. No. 4,565,647, U.S. Pat. No. 5,720,964, and U.S. Pat. No. 5,858,948. In addition, suitable surfactants are also described in *McCutcheon's Emulsifiers and Detergents* (North American and International Editions, by Schwartz, Perry and Berch).

In one embodiment, the composition is free of alkoxylated surfactants. In another embodiment, the composition is free of sulfate based surfactants. By free, it is meant that the composition includes no more than 0.001% of surfactants of this type.

In one aspect, the amphoteric surfactant is selected from an alkyl betaine, an alkylamino betaine, an alkylamido betaines, and mixtures thereof. Representative betaines include lauryl betaine, lauramidopropyl betaine, coco betaine, cocoamidopropyl betaine, cocoamidopropylhydroxy sultaine, sodium lauroamphoacetate, sodium cocoamphoacetate, mono- and di-sodium cocoamphodiacetate, mono- and di-sodium lauroamphodiacetate, sodium cocoamphopropionate, sodium cocoampho hydroxypropyl sulfonate and mixtures thereof.

In one aspect, the anionic surfactant is selected from sodium or ammonium lauryl sulfate, sodium cocoamphoacetate (SCAA), disodium lauryl sulfosuccinate (DSLSS), disodium laureth sulfosuccinate, ammonium or sodium cocoyl isethionate, sodium lauroyl lactylate, sodium cocoyl glutamate, cocoyl glutamate, lauroyl glutamate, capryloyl glutamate, sodium lauroyl sarcosinate, and combinations thereof.

Other Additives

The aqueous surfactant-based composition may optionally include one or more additives, such as one or more of inorganic salts (as noted above), silicones, emollients, emulsifiers, pearlescent agents, coloring agents, particulates, preservatives, pH adjusting agents, botanicals, chelating agents, antimicrobials, and the like. Additionally, rheology modifiers other than the exemplary rheology modifier may be used, which may serve as suspending polymers.

pH Adjusting Agents

The exemplary aqueous surfactant-based compositions can be formulated at pH ranges from 0.5 to 12. The desired pH for the composition may depend on the specific end product applications. Generally, personal care applications have a desired pH range of 3 to 10 in one aspect and from 3.5 to 7.5 in another aspect.

The pH of the exemplary compositions can be adjusted with any combination of acidic and/or basic pH adjusting agents.

Examples of inorganic bases which can be used to increase the pH include alkali metal hydroxides (especially sodium, potassium), and ammonium hydroxide, and alkali metal salts of inorganic acids, such as sodium borate (borax), sodium phosphate, sodium pyrophosphate, and the like, and mixtures thereof. Examples of organic bases which can be used to increase the pH triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine(2-amino 2-hydroxymethyl-1,3-propanediol), and PEG-15 cocamine. Alternatively, other alkaline materials can be used alone or in combination with the above mentioned inorganic and organic bases. Acidic materials suitable for decreasing the pH include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof.

A combination of acidic and basic pH adjusting agents may be employed.

Buffering agents can be used in the exemplary compositions. Suitable buffering agents include alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

The pH adjusting agent and/or buffering agent is utilized in any amount suitable to obtain and/or maintain a desired pH value in the composition.

Silicones

In one aspect, silicones are utilized as conditioning agents which are commonly used in rinse-off hair conditioner products and in shampoo products, such as the so-called "two-in-one" combination cleansing/conditioning shampoos. In one aspect, the conditioning agent is an insoluble silicone conditioning agent. Typically, the conditioning agent will be mixed in the shampoo composition to form a separate, discontinuous phase of dispersed, insoluble particles (also referred to as droplets). The silicone hair conditioning agent phase can be a silicone fluid and can also include other ingredients, such as a silicone resin, to improve silicone fluid deposition efficiency or to enhance the glossiness of the hair, especially when high refractive index (e.g., above about 1.6) silicone conditioning agents are used. The optional silicone hair conditioning agent phase may include volatile silicone, nonvolatile silicone, or combinations thereof. The silicone conditioning agent particles may comprise volatile silicone, non-volatile silicone, or combinations thereof. In one aspect, non-volatile silicone conditioning agents are utilized. If volatile silicones are present, they will typically be incidental to their use as a solvent or carrier for commercially available forms of non-volatile silicone materials ingredients, such as silicone gums and resins. The silicone hair conditioning agents for use in the exemplary surfactant-based compositions disclosed herein have a viscosity of from about 0.5 to about 50,000,000 centistokes (1 centistokes equals $1 \times 10^{-6}$ m$^2$/s) in one aspect, from about 10 to about 30,000,000 centistokes in another aspect, from about 100 to about 2,000,000 in a further aspect, and from about 1,000 to about 1,500,000 centistokes in a still further aspect, as measured at 25° C.

In one embodiment, the silicone conditioning agent particles can have a volume average particle diameter ranging from about 0.01 μm to about 500 μm. For small particle application to hair, the volume average particle diameters can range from about 0.01 μm to about 4 μm in one aspect, from about 0.01 μm to about 2 μm in another aspect, and from about 0.01 μm to about 0.5 μm in still another aspect. For larger particle application to hair, the volume average particle diameters typically range from about 5 μm to about 125 μm in one aspect, from about 10 μm to about 90 μm in another aspect, from about 15 μm to about 70 μm in still another aspect, and from about 20 μm to about 50 μm in a further aspect.

Background material on silicones including sections discussing silicone fluids, gums, and resins, as well as manufacture of silicones, is found in Encyclopedia of Polymer Science and Engineering, vol. 15, 2d ed., pp. 204-308, John Wiley & Sons, Inc. (1989). Silicone fluids are generally described as alkylsiloxane polymers. Non-limiting examples of suitable silicone conditioning agents, and optional suspending agents for the silicone, are described in U.S. Reissue Pat. No. 34,584, and U.S. Pat. Nos. 5,104,646; 5,106,609.

Silicone oils include polyalkyl, polyaryl siloxanes, or polyalkylaryl siloxanes which conform to the following formula:

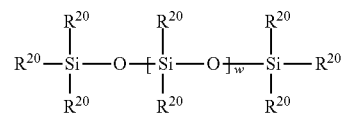

wherein $R^{20}$ is an aliphatic group, independently selected from alkyl, alkenyl, and aryl, $R^{20}$ can be substituted or unsubstituted, and w is an integer from 1 to about 8,000. Suitable unsubstituted $R^{20}$ groups include, but are not limited to alkoxy, aryloxy, alkaryl, arylalkyl, arylalkenyl, alkamino, and ether-substituted, hydroxyl-substituted, and halogen-substituted aliphatic and aryl groups. Suitable $R^{20}$ groups also include amines, cationic amines, and quaternary ammonium groups.

In one aspect, exemplary $R^{20}$ alkyl and alkenyl substituents include $C_1$-$C_5$ alkyl and $C_1$-$C_5$ alkenyl groups. In another aspect, $R^{20}$ is methyl. The aliphatic portions of other alkyl- and alkenyl-containing groups (such as alkoxy, alkaryl, and alkamino) can be straight or branched chains, and contain from $C_1$-$C_5$ in one aspect, from $C_1$-$C_4$ in another aspect, and from $C_1$-$C_2$ in a further aspect. As discussed above, the $R^{20}$ substituents can also contain amino functionalities (e.g., alkamino groups), which can be primary, secondary or tertiary amines or quaternary ammonium. These include mono-, di- and tri-alkylamino and alkoxyamino groups, wherein the aliphatic portion chain length is as described above. Exemplary aryl groups in the foregoing embodiments include phenyl and benzyl.

Exemplary siloxanes are polydimethyl siloxane, polydiethylsiloxane, and polymethylphenylsiloxane. These siloxanes are available, for example, from Momentive Performance Materials in their Viscasil R and SF 96 series, and from Dow Corning marketed under the Dow Corning 200 series. Exemplary polyalkylaryl siloxane fluids that may be used include, for example, polymethylphenylsiloxanes. These siloxanes are available, for example, from Momentive Performance Materials as SF 1075 methyl phenyl fluid, from Dow Corning as 556 Cosmetic Grade Fluid, or from Wacker Chemical Corporation, Adrian, Mich., under the trade name Wacker-Belsil® PDM series of phenyl modified silicones (e.g., PDM 20, PDM 350 and PDM 1000).

Cationic silicone fluids are also suitable for use with the exemplary compositions. Exemplary cationic silicone fluids can be represented by the general formula:

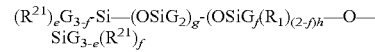

wherein G is hydrogen, phenyl, hydroxy, or $C_1$-$C_8$ alkyl (e.g., methyl or phenyl); e is 0 or an integer having from 1 to 3; f is 0 or 1; g is a number from 0 to 1,999; h is an integer from 1 to 2,000 in one aspect, and from 1 to 10 in another aspect; the sum of g and h is a number from 1 to 2,000 in one aspect, and from 50 to 500 in another aspect; $R^{21}$ is a monovalent radical conforming to the general formula $C_qH_{2q}L$, wherein q is an integer having a value from 2 to 8 and L is selected from the following groups:
a) —N($R^{22}$)$CH_2CH_2$N($R^{22}$)$_2$
b) —N($R^{22}$)$_2$
c) —N$^+$($R^{22}$)$_3$CA$^-$
d) —N($R^{22}$)$CH_2CH_2$N$^+$H$_2$$R^{22}$CA$^-$ wherein $R^{22}$ is independently selected from hydrogen, $C_1$-$C_{20}$ alkyl, phenyl, benzyl; and CA$^-$ is a halide counter ion selected from chloride, bromide, fluoride, and iodide.

In another aspect, a cationic silicone useful in the surfactant-based compositions can be represented by the formula:

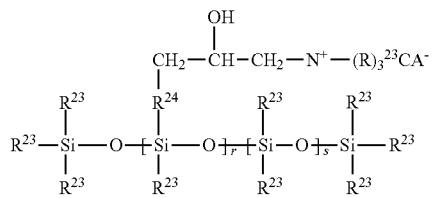

wherein $R^{23}$ represents a radical selected from a $C_1$-$C_{18}$ alkyl and $C_1$-$C_{18}$ alkenyl group; $R^{24}$ independently represents a radical selected from a $C_1$-$C_{18}$ alkylene radical or a $C_1$-$C_{18}$ alkyleneoxy radical; CA is a halide ion; r represents an integer ranging from 2 to 20 in one aspect, and from 2 to 8 in another aspect; s represents an integer ranging from 20 to 200 in one aspect, and from 20 to 50 in another aspect. In one aspect, $R^{23}$ is methyl. In another aspect, Q is a chloride ion. An example of a quaternary silicone polymer useful herein is Abil® T Quat 60, available from Evonik Goldschmidt Corporation, Hopewell, Va.

Another class of suitable silicone fluids is the insoluble silicone gums. These gums are polysiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54, and SE 76. The silicone gums typically have a mass molecule weight in excess of about 200,000 daltons, generally between about 200,000 to about 1,000,000 daltons, specific examples of which include polydimethylsiloxane, polydimethylsiloxane/methylvinylsiloxane copolymer, polydimethylsiloxane/diphenyl siloxane/methylvinylsiloxane) copolymer, and mixtures thereof.

Another category of nonvolatile, insoluble silicone fluid conditioning agents includes high refractive index polysiloxanes, having a refractive index of at least about 1.46 in one aspect, at least about 1.48 in another aspect, at least about 1.52 in a further aspect, and at least about 1.55 in a still further aspect. The refractive index of the polysiloxane fluid will generally be less than about 1.70, typically less than about 1.60. In this context, polysiloxane "fluid" includes oils, resins, and gums.

The high refractive index polysiloxane fluid includes those represented by the general formula set forth for the polyalkyl, polyaryl, and polyalkylaryl siloxanes described above, as well as cyclic polysiloxanes (cyclomethicones) represented by the formula:

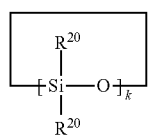

wherein the substituent $R^{20}$ is as defined above, and the number of repeat units, k, ranges from about 3 to about 7 in one aspect, and from 3 to 5 in another aspect. The high refractive index polysiloxane fluids can contain an amount of aryl containing $R^{20}$ substituents sufficient to increase the refractive index to a desired level, which is described above. Additionally, $R^{20}$ and k must be selected so that the material is non-volatile. Aryl containing substituents include those which contain alicyclic and heterocyclic five and six member aryl rings and those which contain fused five or six member rings. The aryl rings can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g., phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

The high refractive index polysiloxane fluids can have a degree of aryl containing substituents of at least about 15% by weight in one aspect, at least about 20% by weight in another aspect, at least about 25% by weight in a further aspect, at least about 35% by weight in still further aspect, and at least about 50% by weight in an additional aspect, based on the weight of the polysiloxane fluid. Typically, the degree of aryl substitution will be less than about 90% by weight, more typically less than about 85% by weight, and can generally range from about 55% to about 80% by weight of the polysiloxane fluid.

In another aspect, the high refractive index polysiloxane fluids have a combination of phenyl or substituted phenyl derivatives. The substituents can be selected from $C_1$-$C_4$ alkyl (e.g., methyl), hydroxy, and $C_1$-$C_4$ alkylamino.

When high refractive index silicones (silicone resins, silicone waxes, and phenyl modified silicones) are used in the exemplary surfactant-based compositions, they optionally can be used in solution with a spreading agent, such as a silicone resin or a suitable surfactant, to reduce the surface tension by a sufficient amount to enhance spreading and thereby augment the glossiness (subsequent to drying) of hair treated with such compositions. Silicone fluids suitable for use in the exemplary surfactant-based compositions are disclosed in U.S. Pat. Nos. 2,826,551; 3,964,500; 4,364,837, and British Patent No. 849,433. High refractive index polysiloxanes and polyaryl siloxanes (trimethyl pentaphenyl trisiloxane, available under the trade name DC PH-1555 HRI) are available from Dow Corning Corporation (Midland, Mich.), Huls America (Piscataway, N.J.), and Momentive Performance Materials Inc. (Albany, N.Y.). Examples of silicone waxes include SF 1632 (INCI Name: Ceteryl Methicone) and SF1642 (INCI Name: C30-45 Alkyl Dimethicone), also available from Momentive Performance Materials, Inc.

Silicone resins and resin gels can be included as a silicone conditioning agent suitable for use in the exemplary surfactant-based compositions. These resins are crosslinked polysiloxanes. The crosslinking is introduced through the incorporation of trifunctional and tetra-functional silanes with monofunctional and/or difunctional silanes during manufacture of the silicone resin.

As is well understood in the art, the degree of crosslinking that is required in order to result in a silicone resin will vary according to the specific silane units incorporated into the silicone resin. In general, silicone materials which have a sufficient level of trifunctional and tetra-functional siloxane monomer units (and hence, a sufficient level of crosslinking) such that they form a rigid or hard film are considered to be silicone resins. The ratio of oxygen atoms to silicon atoms is indicative of the level of crosslinking in a particular silicone material. Silicone materials, which have at least about 1.1 oxygen atoms per silicon atom, will generally be silicone resins herein. In one aspect, the ratio of oxygen: silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and terachlorosilane, with the methyl-substituted silanes being most commonly utilized. In one aspect, suitable silicone resins are SS4230 (INCI Name: Cyclopetasiloxane (and) Trimethylsiloxysilicate) and SS4267 (INCI Name: Dimethicone (and) Trimethylsiloxysilicate) available from Momentive Performance Materials, Inc. Suitable silicone resin gels include RG100 (INCI Name: Cyclopetasiloxane (and) dimethicone/vinyltrimethylsiloxysilicate crosspolymer) from Wacker Chemical Corporation.

Silicone materials and silicone resins can be identified according to a shorthand nomenclature system known as the "MDTQ" nomenclature. Under this naming system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and are specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

Exemplary silicone resins for use in the compositions of the exemplary surfactant-based compositions include, but are not limited to MQ, MT, MTQ, MDT and MDTQ resins. In one aspect, methyl is the silicone resin substituent. In another aspect, the silicone resin is selected from a MQ resins, wherein the M:Q ratio is from about 0.5:1.0 to about 1.5:1.0 and the average molecular weight of the silicone resin is from about 1000 to about 10,000 daltons.

When employed with non-volatile silicone fluids having a refractive index below 1.46, the weight ratio of the non-volatile silicone fluid to the silicone resin component, ranges from about 4:1 to about 400:1 in one aspect, from about 9:1 to about 200:1 in another aspect, from about 19:1 to about 100:1 in a further aspect, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e., the conditioning active, the sum of the fluid and resin should be included in determining the level of silicone conditioning agent in the composition.

The volatile silicones described above include cyclic and linear polydimethylsiloxanes, and the like. As described previously in the formula for cyclic polysiloxanes (cyclomethicones), they typically contain about 3 to about 7 silicon atoms, alternating with oxygen atoms, in a cyclic ring structure. However, each $R^{20}$ substituent and repeating unit, k, in the formula is selected so that the compound is non-volatile. Typically, the $R^{20}$ substituent is substituted with two alkyl groups (e.g., methyl groups). The linear volatile silicones are silicone fluids, as described above, having viscosities of not more than about 25 mPa·s. "Volatile" means that the silicone has a measurable vapor pressure, or a vapor pressure of at least 2 mm of Hg at 20° C. Non-volatile silicones have a vapor pressure of less than 2 mm Hg at 20° C. A description of cyclic and linear volatile silicones is found in Todd and Byers, "Volatile Silicone Fluids for Cosmetics," Cosmetics and Toiletries, Vol. 91(1), pp. 27-32 (1976), and in Kasprzak, "Volatile Silicones," Soap/Cosmetics/Chemical Specialties, pp. 40-43 (December 1986).

Exemplary volatile cyclomethicones include D4 cyclomethicone(octamethylcyclotetrasiloxane), D5 cyclomethicone (decamethylcyclopentasiloxane), D6 cyclomethicone(dodecamethylcyclohexasiloxane), and blends thereof (e.g., D4/D5 and D5/D6). Volatile cyclomethicones and cyclomethicone blends are commercially available from Momentive Performance Materials Inc. as SF1202, SF 1214, SF1256, and SF1258, Dow Corning, Midland, Mich. under the Xiameter® cyclomethicone fluid product designations PMX-0244, PMX-245, PMX-246, PMX-345, and Dow Corning® 1401 fluid. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning as Xiameter® PMX-200 silicone fluids (e.g., product designations 0.65 CS, 1 CS, 1.5 CS, and 2 CS) and Xiameter® PMX 2-1184 silicone fluid.

Emulsified silicones are also suitable for use in the exemplary surfactant-based compositions. In one aspect, suitable emulsified silicones are emulsions of dimethicone with at least one emulsifier selected from nonionic, anionic, amphoteric, cationic surfactant, and/or cationic polymer and mixtures thereof. In one aspect, useful silicone emulsions have an average silicone particle size in the composition of less than 30 µm, less than 20 µm in another aspect, and less than 10 µm in a further aspect. In another aspect, the average silicone particle size of the emulsified silicone in the composition is less than 2 µm, and in another it ranges from 0.01 to 1 µm. Silicone emulsions having an average silicone particle size of <0.15 µm are generally termed microemulsions. Particle size may be measured by means of a laser light scattering technique, using a 2600D Particle Sizer from Malvern Instruments. Suitable silicone emulsions for use in the exemplary surfactant-based compositions are also commercially available in a pre-emulsified form. Examples of suitable pre-formed commercially available emulsions include Dow Corning® emulsions MEM-1664, 2-1352, MEM-1764, MEM-1784, HMW 2220, 2-1865, MEM-1310, MEM-1491, and 5-7137. These are emulsions/microemulsions of dimethiconol. Preformed emulsions of amino functional silicone are also available from suppliers of silicone oils such as Dow Corning (CE-8170, 5-7113, 2-8194, 949, and CE 8401) and Momentive Performance Materials. Particularly suitable are emulsions of amino functional silicone oils with nonionic and/or cationic surfactant. Examples include Dow Corning® 939 cationic emulsion, 949 cationic emulsion, 2-8194 cationic microemulsion, and 2-8299 cationic emulsion, and 2-8177 nonionic emulsion; as well as SM2115 and SME253, nonionic microemulsions supplied by Momentive Performance Materials. Mixtures of any of the above types of silicone may also be used. Other examples of amino functional silicones are the aminosilicone oils. Suitable commercially available aminosilicone oils include Dow Corning® Q2-8166, Q2-8220, and 2-8566; and SF 1708, (Momentive Performance Materials).

Other suitable silicone oils include the dimethicone copolyols, which are linear or branched copolymers of dimethylsiloxane (dimethicone) modified with alkylene oxide units. The alkylene oxide units can be arranged as random or block copolymers. A generally useful class of dimethicone polyols includes block copolymers having terminal and/or pendent blocks of polydimethylsiloxane and blocks of polyalkylene oxide, such as blocks of polyethylene oxide, polypropylene oxide, or both. Dimethicone copolyols can be water soluble or insoluble depending on the amount of polyalkylene oxide present in the dimethicone polymer and can be anionic, cationic, or nonionic in character.

Water soluble or water dispersible silicones can also be used in the exemplary surfactant-based compositions. Such water soluble silicones contain suitable anionic functionality, cationic functionality, and/or nonionic functionality to render the silicone water soluble or water dispersible. In one aspect, the water soluble silicones contain a polysiloxane main chain to which is grafted at least one anionic moiety. The anionic moiety can be grafted to a terminal end of the polysiloxane backbone, or be grafted as a pendent side group, or both. By anionic group is meant any hydrocarbon moiety that contains at least one anionic group or at least one group that can be ionized to an anionic group following neutralization by a base. As discussed previously, the quantity of the hydrocarbon groups of anionic character which are grafted onto the silicone chain are chosen so that the corresponding silicone derivative is water-soluble or water-dispersible after neutralization of the ionizable groups with a base. The anionic silicone derivatives can be selected from existing commercial products or can be synthesized by any means known in the art. The nonionic silicones contain alkylene oxide terminal and/or pendent side chain units (e.g., the dimethicone copolyols discussed above). Another example of nonionic silicones is the silicone polyglucosides from Wacker (e.g., Wacker-Belsil® SPG 128 VP, SPG 130 VP, and VSR 100 VP).

Silicones with anionic groups can be synthesized by reaction between (i) a polysiloxane containing a silinic hydrogen and (ii) a compound containing olefinic unsaturation that also contains an anionic functional group. Exemplary of such a reaction is the hydrosilylation reaction between poly(dimethylsiloxanes) containing a Si—H group(s) and an olefin, $CH_2=CHR^{27}$, wherein $R^{27}$ represents a moiety containing an anionic group. The olefin can be monomeric, oligomeric or polymeric. Polysiloxane compounds that contain a pendent reactive thio (—SH) group(s) are also suitable for grafting an unsaturated anionic group containing compound to the poly(siloxane) backbone.

According to one aspect, the anionic monomers containing ethylenic unsaturation are used alone or in combination and are selected from linear or branched, unsaturated carboxylic acids. Exemplary unsaturated carboxylic acids are acrylic acid, methacrylic acid, maleic acid, maleic anhydride, itaconic acid, fumaric acid and crotonic acid. The monomers can optionally be partially or completely neutralized by base to form an alkali, alkaline earth metal, or ammonium salt. Suitable bases include but are not limited to the alkali, alkaline earth (e.g., sodium, potassium, lithium, magnesium, calcium) and ammonium hydroxides. It will be noted that, similarly, the oligomeric and polymeric graft segments formed from the forgoing monomers can be post-neutralized with a base (sodium hydroxide, aqueous ammonia, etc.) to form a salt. Examples of such silicone derivatives which are suitable for use in the exemplary surfactant-based compositions are described in European Patent Application No. EP 0 582 152 and International Patent Application Pub. No. WO 93/23009. An exemplary class of silicone polymers includes polysiloxanes containing repeat units represented by the following structure:

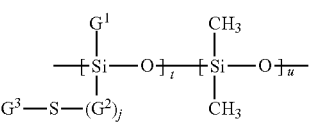

wherein $G^1$ represents hydrogen, $C_1$-$C_{10}$ alkyl, or phenyl radical; $G^2$ represents $C_1$-$C_{10}$ alkylene; $G^3$ represents an anionic polymeric residue obtained from the polymerization of at least one anionic monomer containing ethylenic unsaturation; j is 0 or 1; t is an integer ranging from 1 to 50; and u is an integer from 10 to 350. In one embodiment, $G^1$ is methyl; j is 1; and $G_2$ is propylene radical; $G^3$ represents a polymeric radical obtained from the polymerization of at least one unsaturated monomer containing a carboxylic acid group (e.g., acrylic acid, methacrylic acid, itaconic acid, fumaric acid, crotonic acid, maleic acid, or aconitic acid, and the like).

In one aspect, the carboxylate group content in the final polymer ranges from 1 mole of carboxylate per 200 g of polymer to 1 mole of carboxylate per 5000 g of polymer. In one aspect, the number average molecular weight of the silicone polymer ranges from about 10,000 to about 1,000,000 daltons, and from 10,000 to 100,000 daltons in another aspect. Exemplary unsaturated monomers containing carboxylic acid groups are acrylic acid and methacrylic acid. In addition, to the carboxylic acid group containing monomers, $C_1$-$C_{20}$ alkyl esters of acrylic acid and methacrylic acid can be copolymerized into the polymeric backbone. Exemplary esters may include the ethyl and butyl esters of acrylic and methacrylic acid. A commercially available silicone-acrylate polymer is marketed by the 3M Company under the trademark Silicones "Plus" Polymer 9857C (VS80 Dry). These polymers contain a polydimethylsiloxane (PDMS) backbone onto which is grafted (through a thiopropylene group) random repeating units of poly(meth)acrylic acid and the butyl ester of poly(meth)acrylate. These products can be obtained conventionally by radical copolymerization between thiopropyl functionalized polydimethylsiloxane and a mixture of monomers comprising (meth)acrylic acid and of butyl(meth)acrylate.

In another aspect, the water soluble silicone copolyol useful in the exemplary surfactant-based compositions is selected from silicone copolyol carboxylates represented by the formula:

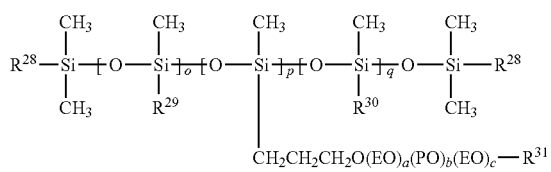

wherein $R^{28}$ and $R^{29}$ are independently selected from $C_1$-$C_{30}$ alkyl, $C_6$-$C_{14}$ aryl, $C_7$-$C_{15}$ aralkyl, $C_1$-$C_{15}$ alkaryl, or an alkenyl group of 1 to 40 carbons, hydroxyl, —$R^{32}$-G' or —$(CH_2)_3O(EO)_a(PO)_b(EO)_c$-G', with the proviso that both $R^{28}$ and $R^{29}$ are not methyl; $R^{30}$ is selected from $C_1$-$C_5$ alkyl or phenyl; in this formula a, b, and c are integers independently ranging from 0 to 100; EO is ethylene oxide, —$(CH_2CH_2O)$—; PO is propylene oxide, —$(CH_2CH(CH_3)O)$—; in this formula o is an integer ranging from 1 to 200, p is an integer ranging from 0 to 200, and q is an integer ranging from 0 to 1000; $R^{31}$ is hydrogen, $C_1$-$C_{30}$ alkyl, aryl, $C_7$-$C_{15}$ aralkyl, $C_7$-$C_{15}$ alkaryl, or alkenyl group of 1 to 40 carbons or —C(O)—X wherein X is $C_1$-$C_{30}$ alkyl, $C_6$-$C_{14}$ aryl, $C_7$-$C_{15}$ aralkyl, $C_1$-$C_{15}$ alkaryl, or an alkenyl group of 1 to 40 carbons, or a mixture thereof; $R^{32}$ is a divalent group selected from alkylene radical of 1 to 40 carbon atoms which may be interrupted with arylene group of 6 to 18 carbons or an alkylene group containing unsaturation of 2 to 8 carbons; and G' is independently selected from a moiety represented by the formula:

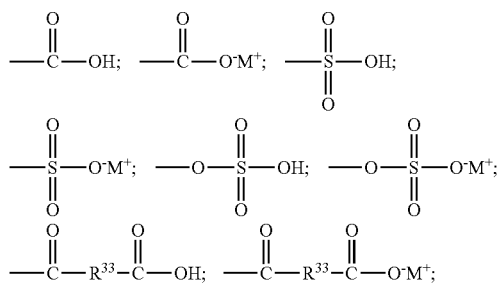

wherein $R^{33}$ is a divalent group selected from alkylene of 1 to 40 carbons, an unsaturated group containing 2 to 5 carbon atoms, or an arylene group of 6 to 12 carbon atoms; M is a cation selected from Na, K, Li, $NH_4$, or an amine containing at least one $C_1$-$C_{10}$ alkyl, $C_6$-$C_{14}$ aryl (e.g., phenyl, naphthyl), $C_2$-$C_{10}$ alkenyl, $C_1$-$C_{10}$ hydroxyalkyl, $C_7$-$C_{24}$ arylalkyl or $C_7$-$C_{24}$ alkaryl groups. Representative $R^{33}$ radicals are: —$CH_2CH_2$—, —CH=CH—, —CH=$CHCH_2$—, and phenylene.

In another embodiment, the water soluble silicones useful in exemplary surfactant-based compositions can be represented an anionic silicone copolyol represented by the formula:

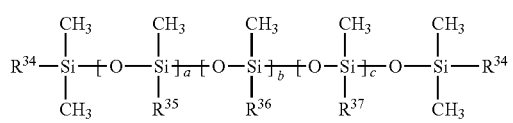

wherein is $R^{34}$ is methyl or hydroxyl; $R^{35}$ is selected from $C_1$-$C_8$ alkyl and phenyl; $R^{36}$ represents the radical —$(CH_2)_3O(EO)_x(PO)_y(EO)_z$—$SO_3^-M^+$; where M is a cation selected from Na, K, Li, and $NH_4$; in this formula x, y and z are integers independently ranging from 0 to 100; $R^{37}$ represents the radical —$(CH_2)_3O(EO)_x(PO)_y(EO)_z$—H; in this formula a and c independently represent integers ranging from 0 to 50, and b is an integer ranging from 1 to 50; EO is ethylene oxide, e.g., —$(CH_2CH_2O)$—; PO is propylene oxide, e.g., —$(CH_2CH(CH_3)O)$—.

In still another embodiment, the water soluble silicones used in exemplary surfactant-based compositions can be represented an anionic silicone copolyol represented by the formula:

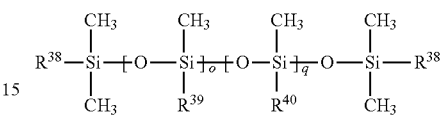

wherein $R^{38}$ and $R^{39}$ independently are —$CH_3$ or a radical represented by: —$(CH_2)_3O(EO)_a(PO)_b(EO)_c$—C(O)—$R^{41}$—C(O)OH, subject to the proviso that both $R^{38}$ and $R^{39}$ are not —$CH_3$ at the same time; $R^{41}$ is selected from the divalent radical —$CH_2CH_2$—, —CH=CH—, and phenylene; $R^{40}$ is selected from $C_1$-$C_5$ alkyl and phenyl; in this formula a, b and c are integers independently ranging from 0 to 20; EO is an ethylene oxide residue, e.g., —$(CH_2CH_2O)$—; PO is a propylene oxide residue, e.g., —$(CH_2CH(CH_3)O)$—; in this formula o is an integer ranging from 1 to 200 and q is an integer ranging from 0 to 500.

Other useful water soluble silicones are quaternized silicone copolyol polymers. These polymers have a pendent quaternary nitrogen functional group present and are represented by the formula:

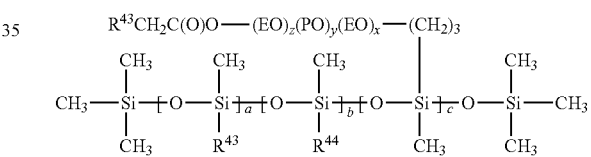

wherein $R^{42}$ represents a quaternary substituent —$N^+R^{45}R^{46}R^{47}CA^-$, wherein $R^{45}$ and $R^{46}$, and $R^{47}$, independently, are selected from hydrogen and linear and branched $C_1$-$C_{24}$ alkyl, and $CA^-$ represents a counter anion suitable to balance the cationic charge on the nitrogen atom; $R^{43}$ is selected from $C_1$-$C_{10}$ alkyl and phenyl; $R^{44}$ is —$(CH_2)_3$ $O(EO)_x(PO)_y(EO)_z$—H, where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20. In one aspect, the counter anion $CA^-$ represents an anion selected from chloride, bromide, iodide, sulfate, methylsulfate, sulfonate, nitrate, phosphate, and acetate.

Other suitable water soluble silicones are amine substituted silicone copolyols represented by the formula:

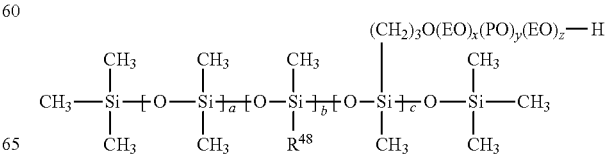

wherein $R^{48}$ is selected from —NH(CH$_2$)$_n$NH$_2$ and —(CH$_2$)$_n$NH$_2$; in this formula n is an integer from 2 to 6; and x, is n integer from 0 to 20; where EO is an ethylene oxide residue, e.g., —(CH$_2$CH$_2$O)—; PO is a propylene oxide residue, e.g., —(CH$_2$CH(CH$_3$)O)—; in this formula a is an integer from 0 to 200, b is an integer from 0 to 200, and c is an integer from 1 to 200; in this formula x, y and z are integers and are independently selected from 0 to 20.

Still other water soluble silicones can be selected from nonionic silicone copolyols (dimethicone copolyols) represented by the formula:

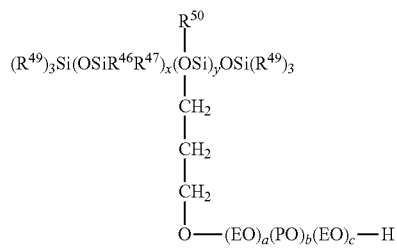

wherein each $R^{49}$ independently represents a radical selected from C$_1$-C$_{30}$ alkyl, C$_6$-C$_{14}$ aryl, and C$_2$-C$_{20}$ alkenyl; $R^{50}$ represents a radical selected from C$_1$-C$_{30}$ alkyl, C$_6$-C$_{14}$ aryl, and C$_2$-C$_{20}$ alkenyl; EO is an ethylene oxide residue, e.g., —(CH$_2$CH$_2$O)—; PO is a propylene oxide residue, e.g., —(CH$_2$CH(CH$_3$)O)—; in this formula a, b, and c are independently 0 to 100; in this formula x is 0 to 200; and y is 1 to 200.

In another embodiment, water soluble silicones can be selected from nonionic silicone copolyols represented by the formula:

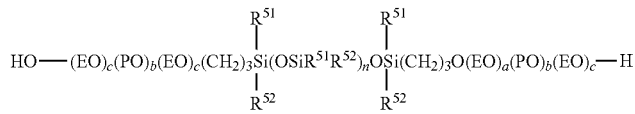

wherein $R^{51}$ and $R^{52}$ independently represent a radical selected from C$_1$-C$_{30}$ alkyl, C$_6$-C$_{14}$ aryl, and C$_2$-C$_{20}$ alkenyl; EO is an ethylene oxide residue, e.g., —(CH$_2$CH$_2$O)—; PO is a propylene oxide residue, e.g., —(CH$_2$CH(CH$_3$)O)—; in this formula a, b, and c are independently 0 to 100; and in this formula n is 0 to 200.

In the formulas set forth above, the EO and PO residues can be arranged in random, in nonrandom, or in blocky sequences.

Water soluble silicones are disclosed in U.S. Pat. Nos. 5,136,063 and 5,180,843. Such silicones are commercially available under the Silsoft® and Silwet® trade names from Momentive Performance Materials. Specific product designations include, but are not limited to, Silsoft product designations 430, 440, 475, 805, 810, 840, 870, 875, 880, 895, 900, and 910; Silwet product designation L-7604. Other commercially available products include Dow Corning® 5103 and 5329; Abil® product designations B 88183, B 8843, Evonik Goldschmidt, and Silsense™ dimethicone copolyols, such as Silsense Copolyol-1 and Silsense Copolyol-7, available from Lubrizol Advanced Materials, Inc., Cleveland, Ohio.

The concentration of the silicone agents described above can range from about 0.01% to about 10%, by weight of the surfactant-based. In another aspect, the amount of silicone agent ranges from about 0.1% to about 8%, from about 0.1% to about 5% in still another aspect, and from about 0.2% to about 3% by weight in a further aspect, all based on the total weight of the composition.

Emollients

Suitable emollients may include mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); polyalkylene glycols; lanolin and lanolin derivatives; mixtures thereof, and the like. Silicone fluids (e.g., volatile silicone oils and non-volatile silicone oils as described above), can also serve as emollients.

Mineral oils and petrolatums include cosmetic, USP and NF grades and are commercially available from Penreco under the Drakeol® and Penreco® trade names. Mineral oil includes hexadecane and paraffin oil.

Suitable fatty alcohol emollients include fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof.

Exemplary of the fatty acid and fatty alcohol ester emollients include hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohol emollients are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect, the ethoxylated fatty alcohols can be represented by the formula R'—(OCH$_2$CH$_2$)$_n$—OH, wherein R' represents the aliphatic residue of the parent fatty alcohol and n represents the number of molecules of ethylene oxide. In another aspect, R' is derived from a fatty alcohol containing 8 to 30 carbon atoms. In one aspect, n' is an integer ranging from 2 to 50, 3 to 25 in another aspect, and 3 to 10 in a further aspect. In a still further aspect, R' is derived from a fatty alcohol emollient set forth above. Exemplary ethoxylated fatty alcohols include capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. The propoxylated adducts of the foregoing fatty alcohols and mixed ethoxylated/propoxylated adducts of the foregoing fatty alcohols are also contemplated. The ethylene oxide and propylene oxide units of the ethoxylated/propoxylated fatty alcohols can be arranged in random or in blocky order.

More specific examples of ethoxylated alcohols include Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols include PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols include PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acid emollients are formed when a fatty acid is reacted with an alkylene oxide or with a pre-formed polymeric ether. The resulting product may be a monoester, diester, or mixture thereof. Suitable ethoxylated fatty acid ester emollients suitable for use herein are products of the addition of ethylene oxide to fatty acids. The product is a polyethylene oxide ester of a fatty acid. In one aspect, the ethoxylated fatty acid esters can be represented by the formula $R''-C(O)O(CH_2CH_2O)_{n''}-H$, wherein $R''$ represents the aliphatic residue of a fatty acid and n represents the number of molecules of ethylene oxide. In another aspect, $n''$ is an integer ranging from 2 to 50, 3 to 25 in another aspect, and 3 to 10 in a further aspect. In still another aspect, $R''$ is derived from a fatty acid containing 8 to 24 carbon atoms. In a still further aspect, $R''$ is derived from a fatty acid emollient as set forth above. It is to be recognized that propoxylated and ethoxylated/propoxylated products of the foregoing fatty acids are also contemplated. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Guerbet ester emollients are formed from the esterification reaction of a Guerbet alcohol with a carboxylic acid. Guerbet ester emollients are commercially available from Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from Lubrizol Advanced Materials, Inc. under the trade names Lanolin LP 108 USP, Lanolin USP AAA, Acetulan™ Ceralan™, Lanocerin™, Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P).

The emollient(s) (exclusive of silicones discussed above) can be utilized in an amount ranging from about 0.5 wt. % to about 30 wt. % by weight of the total personal care composition in one aspect 0.1 wt. % to 25 wt. % in another aspect, and 5 wt. % to 20 wt. % in a further aspect. While emollients are generally employed in personal care compositions, they can be employed in home care, health care, and institutional care compositions in the same wt. ratios as set forth for personal care compositions so long as they effect a desired physical attribute (e.g., humectant properties) in such compositions.

Pearlescent Agents

Some formulations are opacified by deliberately incorporating pearlescent materials therein to achieve a cosmetically attractive pearl-like appearance, known as pearlescence. An opacifier often is included in a composition to mask an undesirable aesthetic property, such as to improve the color of a composition that is darkened due to the presence of a particular ingredient, or to mask the presence of particulate matter in the composition. Opacifiers also are included in aqueous compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and pearling agents in shampoos" by Hunting, *Cosmetic and Toiletries*, Vol. 96, pages 65-78 (July 1981). The opacifying or pearlescent material may include one or more of ethylene glycol mono-stearate, ethylene glycol distearate, polyethylene glycol distearate, stearic alcohol, bismuth oxychloride coated mica, mica coated metal oxides (e.g., titanium dioxide, chromium oxide, iron oxides), myristyl myristate, guanine, glitter (polyester or metallic), aluminum and magnesium salts, and organic compounds, like fatty alcohols, fatty esters and various polymers and copolymers and mixtures thereof. Other pearlescent/opacifying materials can be found in U.S. Pat. Nos. 4,654,207; 5,019,376; and 5,384,114, and in the CTFA Cosmetic Ingredient Handbook, J. Nikitakis, ed., The Cosmetic, Toiletry and Fragrance Association, Inc., Washington, D.C., 1988, at page 75.

In one aspect, the amount of the pearlescent/opacifying material in the aqueous surfactant-based composition can range from 0.05 wt. % to 10 wt. %, or from 0.1 wt. % to 3 wt. %.

Colorants

Colorants include pigments and dyes. Exemplary pigments and dyes include metal compounds or semi-metallic compounds and may be used in ionic, nonionic or oxidized form. The pigments can be in this form either individually or in admixture or as individual mixed oxides or mixtures thereof, including mixtures of mixed oxides and pure oxides. Examples include titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxide, zirconium oxides (e.g., $ZrO_2$), barium sulfate ($BaSO_4$), and mixtures thereof.

Other examples of pigments include D&C Red No. 30, D&C Red No. 36, D&C Orange No. 17, Green 3 Lake, Ext. Yellow 7 Lake, Orange 4 Lake, Red 28 Lake, the calcium lakes of D&C Red Nos. 7, 11, 31 and 34, the barium lake of D&C Red No. 12, the strontium lake D&C Red No. 13, the aluminum lakes of FD&C Yellow No. 5 and No. 6, the aluminum lakes of FD&C No. 40, the aluminum lakes of D&C Red Nos. 21, 22, 27, and 28, the aluminum lakes of FD&C Blue No. 1, the aluminum lakes of D&C Orange No. 5, the aluminum lakes of D&C Yellow No. 10; the zirconium lake of D&C Red No. 33, iron oxides, thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles and the like. Other suitable pigments include various optical modifiers as described in U.S. Pat. No. 7,202,199.

Particulates, Other than Pigments

Numerous cosmetically useful particulate exfoliating agents are known in the art, and the selection and amount is determined by the exfoliating effect desired from the use of the composition, as recognized by those skilled in the cosmetic arts. Useful exfoliating agents include natural abrasives, inorganic abrasives, synthetic polymers, and the like, and mixtures thereof. Representative exfoliants include ground or powdered pumice, stone, zeolites, nut shells (e.g., almond, pecan, walnut, coconut, and the like), nut meals (e.g., almond, and the like), fruit pits (e.g., apricot, avocado, olive, peach, and the like), hulls, seed and kernel (e.g., oat bran, corn meal, rice bran, grape seed, kiwi seed, wheat, jojoba seed, loofah seed, rose hip seed, and the like), plant matter (e.g., tea tree leaves, corn cob, fruit fibers, seaweed, loofah sponge, microcrystalline cellulose, and the like), bivalve shells (oyster shell, and the like), calcium carbonate, dicalcium pyrophosphate, chalk, silica, kaolin clay, silicic acid, aluminum oxide, stannic oxide, sea salt (e.g., Dead Sea salt), talc, sugars (e.g., table, brown, and the like), polyethylene, polystyrene, microcrystalline polyamides (nylons), microcrystalline polyesters, polycarbonates, and stainless steel fibers. The foregoing exfoliants can be used in the form of granules, powders, flours, and fibers.

Other generally insoluble components suitable for use in the present compositions include clay, swellable clay, laponite, gas bubbles, liposomes, microsponges, cosmetic beads and flakes. Cosmetic beads, flakes and capsules can be included in a composition for aesthetic appearance or can function as micro- and macro-encapsulants for the delivery of benefit agents to the skin and hair. Exemplary bead components may include agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.).

Any suitable anti-dandruff agent can be employed in the exemplary compositions. Exemplary anti-dandruff agents may include sulfur, zinc pyrithione, zinc omadine, miconazole nitrate, selenium sulfide, piroctone olamine, N, N-bis (2-hydroxyethyl)undecenamide, cade oil, pine tar, *Allium cepa* extract *Picea abies* extract, and Undecyleneth-6, and the like, and mixtures thereof.

In one aspect, the amount of particulate component can range from 0.1 wt. % to 10 wt. % of the composition.

Botanicals

Optionally, the compositions can contain botanical material extracts. Extracted botanical materials can include any water soluble or oil soluble material extracted from a particular plant, fruit, nut, or seed. In one aspect, the antiperspirant compositions the botanical actives are present in an amount ranging from 0.1 wt. % to 10 wt. %, e.g., from 0.5 wt. % to 8 wt. %, or from 1 wt. % to 5 wt. % of the composition.

Suitable botanical agents can include, for example, extracts from *Echinacea* (e.g., sp. *angustifolia, purpurea, pallida*), *yucca glauca*, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts include, for example, chlorogenic acid, glutathione, glycrrhizin, neohesperidin, quercetin, rutin, morin, myricetin, absinthe, and chamomile.

Cationic Polymers and Compounds

Cationic polymers and compounds are useful in the exemplary aqueous surfactant-based compositions. Those of ordinary skill in the art will recognize that many of these cationic agents serve multiple functions. Typically, these agents are useful as conditioners (e.g., hair and skin), antistatic agents, fabric softening, and as antimicrobial agents. Cationic polymers can be synthetically derived or obtained by modifying natural polymers such as the cationically modified polysaccharides and polygalactomannans.

Representative cationic polymers may include homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products Inc., Wayne, N.J.; the dimethyl amino ethyl methacrylate/vinyl caprolactam/vinyl pyrrolidone terpolymers, such as the product sold under the trade name GAFFIX™ VC 713 by International Specialty Products Inc.; the vinyl pyrrolidone/methacrylamidopropyl dimethylamine copolymer, marketed under the trade name STYLEZE™ CC 10 available from International Specialty Products Inc.; and the vinyl pyrrolidone/quaternized dimethyl amino propyl methacrylamide copolymers such as the product sold under the trade name GAFQUAT™ HS 100 by International Specialty Products, Inc.

Cationic agents can also be selected from the quaternary polymers of vinyl pyrrolidone and vinyl imidazole such as the products sold under the trade name Luviquat® (product designation FC 370 and FC 550) by BASF. Other cationic polymer agents that can be used in the compositions include polyalkyleneimines such as polyethyleneimines, polymers containing vinyl pyridine or vinyl pyridinium units, condensates of polyamines and epichlorhydrins, quaternary polysaccharides, quaternary polyurethanes, quaternary silicones, and quaternary derivatives of chitin.

Other non-limiting examples of quaternary ammonium compounds (monomeric and polymeric) useful as cationic agents include acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, Quaternium-22, Quaternium-26, Quaternium-27, Quaternium-52, Quaternium-53, Quaternium-63, Quaternium-70, Quaternium-72, Quaternium-76, hydrolyzed collagen, PEG-2-cocomonium chloride, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, Polyquaternium-1, Polyquaternium-4, Polyquaternium-6, Polyquaternium-7, Polyquaternium-10, Polyquaternium-11, Polyquaternium-15, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium-39, Polyquaternium-44, Polyquaternium-46, Polyquaternium-47, Polyquaternium-52, Polyquaternium-53, Polyquarternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-87, PEG-2-cocomonium chloride; and mixtures thereof.

Other useful cationic polymers include the cationic polygalactomannans (e.g., quaternized derivatives of guar and cassia, such as, guar hydroxypropyl trimmonium chloride, hydroxypropyl guar hydroxypropyl trimmonium chloride, and cassia hydroxypropyl trimmonium chloride).

Cationic agents useful herein may also include proteins and protein derivatives, amines, protonated amine oxides, betaines, and the like. Protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, hydrolyzed wheat protein, hydrolyzed sweet almond protein, hydrolyzed rice protein, hydrolyzed soy protein, hydrolyzed milk protein, hydrolyzed vegetable protein, hydrolyzed keratin, hydrolyzed collagen, hydrolyzed wheat gluten, potassium cocoyl hydrolyzed collagen, hydroxypropyl trimonium hydrolyzed collagen, cocodimonium hydroxypropyl hydrolyzed milk protein, lauryldimonium hydroxypropyl hydrolyzed wheat protein, lauryldimonium hydroxypropyl hydrolyzed collagen, keratin amino acids, collagen amino acids, soyethyldimonium ethosulfate, soyethyl morpholinium ethosulfate, and the like.

The monomeric quaternary ammonium compounds include, for example, alkylbenzyldimethyl ammonium salts, betaines, heterocyclic ammonium salts, and tetraalkylammonium salts. Long-chain (fatty) alkylbenzyldimethyl ammonium salts are utilized as conditioners, as antistatic agents, and as fabric softeners, discussed in more detail below.

Examples of alkylbenzyldimethylammonium salts may include stearalkonium chloride, benzalkonium chloride, Quaternium-63, olealkonium chloride, didecyldimonium chloride, and the like. The betaine compounds include the alkylamidopropyl betaines and the alkylamidopropyl hydroxysultaines, as described in the formulas set forth previously above. Non-limiting examples of alkyl betaine compounds include oleyl betaine, cocobetaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine.

The heterocyclic ammonium salts include the alkylethyl morpholinium ethosulfates, isostearyl ethylimidonium ethosulfate, and the alkylpyridinium chlorides. Non-limiting examples of heterocyclic ammonium salts may include cetylpyridinium chloride, isostearylethylimidonium ethosulfate, and the like.

Non-limiting examples of tetraalkylammonium salts include cocamidopropyl ethyldimonium ethosulfate, hydroxyethyl cetyldimonium chloride, Quaternium-18, and cocodimonium hydroxypropyl hydrolyzed protein, such as hair keratin, and the like.

A number of quaternary ammonium compounds are used as antistatic agents for fabric conditioning and fabric care. They include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, "Fabric Conditioning Agents," HAPPI, pp. 55-58 (February 1995).

Non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, and the like. Non-limiting examples of amidoamine quaternary compounds include N-alkyl-N-methyl-N,N-bis(2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g., natural oil and fatty acid-derived) alkylated quaternary ammonium compounds are suitable fabric softening agents. In one aspect, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, and palmityl groups. Representative compounds include, but not limited, to N,N-di(alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl) ammonium chloride, N, N-di(canolyloxyethyl)-N-methyl-N-(2-hydroxyethyl)ammonium chloride, and the like; N,N-di(2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N,N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N-dimethyl ammonium chloride, N-(2-canoloyloxy-2-ethyl)-N-(2-canolyloxy-2-oxoethyl)-N,N-dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canolyloxy-2-oxoethyl)-N-canolyl-N,N-dimethyl ammonium chloride, and the like.

In another aspect, quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl) ammonium methylsulfate, dialkyl esterquat derivatives of methyltriethanol ammonium salts such as the bis(acyloxyethyl)hydroxyethylmethylammonium methosulfate esterquats, and the like; and N,N-di(tallowoyloxyethyl)-N,N-dimethylammonium chloride, where the tallow chains are at least partially unsaturated.

In a further aspect, fabric softening agents include the well-known dialkyldimethyl ammonium salts such as N,N-ditallowyl-N,N-dimethyl ammonium methylsulfate, N,N-di(hydrogenated-tallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride, N,N-ditallowyl-N,N-dimethyl ammonium chloride, N,N-distearyl-N,N-dimethyl ammonium chloride, N,N-dibehenyl-N,N-dimethyl ammonium chloride, and N,N-dimethyl-N-stearyl-N-benzylammonium chloride.

The foregoing monomeric and polymeric quaternary ammonium salt compounds can have any anionic group as a counter-ion, for example, chloride, bromide, methosulfate (i.e., methylsulfate), acetate, formate, sulfate, nitrate, and the like.

For fabric softening applications, any suitable quaternary ammonium agent can be utilized in combination with the aqueous surfactant-based compositions. For ester-containing fabric softening agents, the pH of the compositions can influence the stability of the fabric softening agents, especially in prolonged storage conditions. The pH, as defined in the present context, is measured in the neat compositions at about 20° C. In one aspect, the pH of the composition is less than about 6. In another aspect, the pH is in the range of from 2 to 5, and from 2.5 to 3.5 in a further aspect.

In one aspect, the cationic agent(s) can be employed in amounts ranging from 0.05 wt. % to 15 wt. %, from 0.1 wt. % to 10 wt. % in another aspect, and from 0.5 wt. % to 3 wt. % in a further aspect, based on the weight of the final composition, but is not limited thereto.

Preservatives

In one aspect, any preservative suitable for use in personal care, home care, health care, and institutional and industrial care products, can be used in the exemplary compositions. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1).

In another aspect, acid based preservatives are useful in the exemplary compositions. The use of acid based preservatives facilitates the formulation of products in the low pH range. Lowering the pH of a formulation inherently provides an inhospitable environment for microbial growth.

Any acid based preservative that is useful in personal care, home care, health care, and institutional and industrial care products can be used in the exemplary compositions. In one aspect the acid preservative is a carboxylic acid compound represented by the formula: $R^{53}C(O)OH$, wherein $R^{53}$ represents hydrogen, a saturated and unsaturated hydrocarbyl group containing 1 to 8 carbon atoms or $C_6$ to $C_{10}$ aryl. In another aspect, $R^{53}$ is selected from a hydrogen, a $C_1$ to $C_8$ alkyl group, a $C_2$ to $C_8$ alkenyl group, or phenyl. Exemplary acids are formic acid, acetic acid, propionic acid, sorbic acid, caprylic acid, and benzoic acid, and mixtures thereof.

In another aspect, suitable acids may include oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above.

The acid based preservatives and/or their salts can be used alone or in combination with non-acidic preservatives typically employed in personal care, home care, health care, and institutional and industrial care products.

The preservatives typically comprise from 0.01% to 3.0% by weight in one aspect, from 0.1% to 1% by weight in another aspect, and from 0.3% to 1% by weight in a further aspect, of the total weight of the exemplary personal care compositions.

The preservatives may also serve as antimicrobial agents for destroying or inhibiting the growth of pathogenic microorganisms and those hazardous to human health which may be present on the skin, when used in pharmaceutically effective amounts.

Auxiliary Rheology Modifier

In addition to the rheology modifier disclosed herein, the surfactant based composition may contain one or more auxiliary rheology modifiers and thickeners. Suitable rheology modifiers and thickeners include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule, wherein in one aspect the substituent is independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053.

In one aspect, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980 and 996 available from Lubrizol Advanced Materials, Inc. In a further aspect, the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814. Some of the forgoing polymers are designated under INCI nomenclature as Acrylates/$C_{10-30}$ Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc.

In another aspect, the auxiliary rheology modifier can be a crosslinked, linear poly(vinyl amide/acrylic acid) copolymer as disclosed in U.S. Pat. No. 7,205,271.

Another class of optional synthetic rheology modifiers and thickeners suitable for use herein includes hydrophobically modified ASTs, commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer," and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843. In addition, an extensive review of HASE polymers is found in Gregory D. Shay, Chapter 25, "Alkali-Swellable and Alkali-Soluble Thickener Technology A Review," Polymers in Aqueous Media—Performance Through Association, Advances in Chemistry Series 223, J. Edward Glass (ed.), ACS, pp. 457-494, Division Polymeric Materials, Washington, D.C. (1989). Commercially available HASE polymers are sold under the trade names, Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer) from Rohm & Haas, and Novethix™ L-10 (INCI Name: Acrylates/Beheneth-25 Methacrylate Copolymer) from Lubrizol Advanced Materials, Inc.

In another embodiment, acid swellable associative polymers can be used herein. Such polymers generally have cationic and associative characteristics. These polymers are free radical addition polymers polymerized from a monomer mixture comprising an acid sensitive amino substituted hydrophilic monomer (e.g., dialkylamino alkyl(meth)acrylates or (meth)acrylamides), an associative monomer (defined hereinabove), a lower alkyl(meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from 0.5 to 6.5. Exemplary acid swellable associative polymers are commercially available under the trade name Structure® Plus (INCI Name: Acrylates/Aminoacrylates/C10-C30 Alkyl PEG-20 Itaconate) from Akzo Nobel, and Carbopol® Aqua CC (INCI Name: Polyacrylates-1 Crosspolymer) from Lubrizol Advanced Materials, Inc. In one aspect, the acid swellable polymer is a copolymer of one or more $C_1$-$C_5$ alkyl esters of (meth)acrylic acid, $C_1$-$C_4$ dialkylamino $C_1$-$C_6$ alkyl meth(acrylate), PEG/PPG-30/5 allyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479.

Hydrophobically modified alkoxylated methyl glucoside, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Glucamate™ SSE-20, respectively, are also suitable as auxiliary rheology modifiers.

Polysaccharides obtained from tree and shrub exudates, such as gum Arabic, gum gahatti, and gum tragacanth, as well as pectin; seaweed extracts, such as alginates and carrageenans (e.g., lambda, kappa, iota, and salts thereof); algae extracts, such as agar; microbial polysaccharides, such as xanthan, gellan, and wellan; cellulose ethers, such as ethylhexylethylcellulose, hydroxybutylmethylcellulose, hydroxyethylmethylcellulose, hydroxypropyl-methylcellulose, methylcellulose, carboxymethylcellulose, hydroxyethylcellulose, and hydroxypropylcellulose; polygalactomannans, such as fenugreek gum, cassia gum, locust bean gum, tara gum, and guar gum; starches, such as corn starch, tapioca starch, rice starch, wheat starch, potato starch and sorghum starch can also be employed in the compositions herein as suitable auxiliary thickeners and rheology modifiers.

A comprehensive list of thickening, viscosifying or rheology modifying chemicals can be found in the International Cosmetic Ingredient Dictionary and Handbook (T. Gottschalk and H. P. Breslawec, "International Cosmetic Ingredient Dictionary and Handbook," pages 3974-3977, 14$^{th}$ Ed, Personal Care Products Council Publisher, Washington, D.C., USA (2012)).

The auxiliary rheology modifiers, when employed, can be used alone or in combination and typically are used in an amount ranging from 0.1 wt. % to 8 wt. % in one aspect, from 0.3 wt. % to 3 wt. % in another aspect, and from 0.5 wt. % to 2 wt. % of the personal care composition.

In one aspect, the aqueous surfactant-based composition contains no more than a total of 0.1 wt. % of all rheology modifiers other than the exemplary rheology modifier.

Emulsifiers

Emulsifiers which may be employed in the exemplary compositions include $C_{12}$-$C_{22}$ fatty alcohols, $C_{12}$-$C_{22}$ alkoxylated alcohols, $C_{12}$-$C_{22}$ fatty acids, $C_{12}$-$C_{22}$ alkoxylated fatty acids (the alkoxylates each having 10 to 80 units of ethylene oxide, propylene oxide, and combinations of ethylene oxide/propylene oxide present in the molecule), $C_8$-$C_{22}$ APGs, ethoxylated sterols (wherein the number of ethylene oxide units ranges from 2 to about 150), partial esters of polyglycerols, esters and partial esters of polyols having 2 to 6 carbon atoms, partial esters of polyglycerols, and organosiloxanes, and combinations thereof.

The $C_8$-$C_{22}$ alkyl APG emulsifiers are prepared by reacting glucose or an oligosaccharide with primary fatty alcohols having 8 to 22 carbon atoms, and comprise a glucosidically bonded $C_8$-$C_{16}$ alkyl group on an oligoglucoside residue whose average degree of oligomerization is 1 to 2. In addition to the APGs described as surfactants above, APGs are available under the trademark Plantacare® (Cognis Corporation, Cincinnati, Ohio). Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Emulsifiers based on the esters and partial esters of polyols having 2 to 6 carbon atoms are condensed with linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

Exemplary fatty alcohols and fatty acids, as well as their alkoxylates, the partial esters of polyglycerols, as well as the organosiloxanes are described above.

Chelating Agents

Chelating agents can be employed to stabilize the personal care, home care, health care, and institutional care compositions disclosed herein against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof. Such suitable chelators typically comprise 0.001 wt. % to 3 wt. %, e.g., 0.01 wt. % to 2 wt. %, or 0.01 wt. % to 1 wt. % of the composition.

Auxiliary Solvents and Diluents

The personal care, home care, health care, and institutional care compositions containing the thickened surfactant compositions in combination with one or more of the foregoing active ingredients and/or with the one or more additives and/or adjuvants, conventionally or popularly included in personal care, health care, home care, and institutional care products discussed above can be prepared as water-based formulations, and formulations containing water-miscible auxiliary solvents and/or diluents, but are not limited thereto.

Useful solvents commonly employed are typically liquids, such as alcohols, fatty alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$ to $C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having 2 to 30 carbon atoms and 1 to 40 alkoxy units, polypropylene glycol, polybutylene glycol, and the like. Non-limiting examples of non-aqueous auxiliary solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents or diluents may also be conditioners and emulsifiers.

Exemplary organic solvents include those listed above, as well as mono-alcohols having 2 to 5 carbon atoms per molecule, such as ethanol. The organic solvent may be present at a concentration of 0.01 wt. % to 20 wt. %, e.g., up to 10 wt. %, such as up to 5 wt. %, and in one embodiment, no more than 1 wt. %.

Propellants

Where desired, any known aerosol propellant can be utilized to deliver the exemplary personal care, home care, health care, and institutional care compositions in combination with one or more of the foregoing active ingredients and/or with the one or more additives and/or adjuvants, conventionally or popularly included in such products. Exemplary propellants may include lower boiling hydrocarbons such as $C_3$-$C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane, and compressed gases, such as air and carbon dioxide.

In one aspect, these compositions can contain from 0.1 wt. % to 60 wt. % by weight of a propellant, or from 0.5 to 35 wt. %.

Exemplary Compositions

The exemplary glycoside esters, such as MeG esters have a variety of end use applications, such as, for example, personal care applications. Typical personal care applications include, for example, pharmaceutical and cosmetic compositions, such as, for example, shampoos, conditioners, ointments, skin creams, lotions, soaps, and the like. Typical household applications include, for example, use as viscosity adjusters for general fluids handling and for surfactant applications, such as, dishwashing liquids, laundry detergents, and the like.

The exemplary thickeners are introduced to the liquid surfactant compositions in liquid form or as a paste and mixed under conditions effective to dissolve the thickener into the liquid surfactant composition and cause significant viscosity increases, e.g., up to 2,000 to 100,000 mPa·s. The ability to introduce the thickener in a liquid form can provide a formulator with a greater degree of accuracy in introducing the correct amount of thickener to the liquid surfactant system and also facilitates automated processing. The thickeners can be used to prepare surfactant formulations e.g., shampoos, at ambient temperatures, e.g., from about 20 to 30° C. (known in the art as "cold processing"). They can be added to the formulations at any step of the process to adjust its viscosity as desired. The glycoside esters can also be added to the surfactant composition at elevated temperatures, via "hot processing," as needed to melt waxes, pearlescent agents and other high melting point formulation adjuvants.

The compositions containing the exemplary rheology modifier can be packaged and dispensed from containers such as jars, tubes, sprays, wipes, roll-ons, sticks and the like, without limitation. There is no limitation as to the form of the product in which the rheology modifier can be incorporated, so long as the purpose for which the product is used is achieved. For example, personal care products containing the exemplary rheology modifier can be applied to the skin, hair, scalp, and nails, without limitation in the form of gels, sprays (liquid or foams), emulsions (creams, lotions, pastes), liquids (rinses, shampoos), bars, ointments, and the like.

Exemplary uses include hair care products (shampoos, combination shampoos, such as "two-in-one" conditioning shampoos), post-shampoo rinses, setting and style maintenance agents (including setting aids, such as gels and sprays, grooming aids such as pomades, conditioners, perms, relaxers, hair smoothing products, and the like), skin care products (facial, body, hands, scalp and feet), such as creams, lotions and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), hair colorants (hair dyes, hair color rinses, highlighters, bleaches and the like), pigmented skin colorants (face and body make-ups, foundation creams, mascara, rouge, lip products, and the like) bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softness, and the like).

Toiletries and beauty aids containing the rheology modifier disclosed herein can include, without limitation, hair-removal products (shaving creams and lotions, epilators, after-shaving skin conditioner, and the like), hair growth promoting products, deodorants and antiperspirants, oral care products (mouth, teeth, gums), such as mouth wash, dentifrice, such as toothpaste, tooth powder, tooth polishes, tooth whiteners, breath fresheners, denture adhesives, and the like; facial and body hair bleach and the like. Other beauty aids that can contain the rheology modifier can include sunless tanning applications containing artificial tanning accelerators, such as dihydroxyacetone (DHA), tyrosine, tyrosine esters and the like: skin depigmenting, whitening and lightening, formulations containing such active ingredients as kojic acid, hydroquinone, arbutin, fruital, vegetable or plant extracts, (lemon peel extract, chamomile, green tea, paper mulberry extract, and the like), ascorbyl acid derivatives ascorbyl palmitate, ascorbyl stearate, magnesium ascorbyl phosphate and the like).

Example Body Wash

In one aspect, a personal care composition in which the exemplary rheology modifier is useful is a body wash. Typical components of a body wash, in addition to the rheology modifier and water include at least one surfactant, a pH adjusting agent (base and/or acid) in sufficient amount to provide the composition with a pH of from about 3.0 to about 7.5 in one aspect, from about 4.0 to about 6.5 in another aspect, and from about 5.0 to about 6.0 in a further aspect. Optional ingredients selected from the additives discussed above, and mixtures thereof, may also be incorporated, such as, for example, silicones, pearlizing agents, vitamins, oils, fragrances, dyes, preservatives including acids, botanicals, exfoliating agents, insoluble gas bubbles, liposomes, microsponges, cosmetic beads flakes, and mixtures thereof. In one aspect, the surfactant is an anionic surfactant. In another aspect, the surfactant is a mixture of an anionic surfactant and an amphoteric surfactant, in optional combination with a non-ionic surfactant. In another aspect, the surfactant is a mixture of an anionic surfactant and an amphoteric surfactant, in optional combination with a cationic and/or a non-ionic surfactant. In one aspect, the anionic surfactant can be present in an amount ranging from about 5% to about 40% by weight, from about 6% to about 30% by weight in another aspect, and from about 8% to about 25% by weight in a further aspect, based on the total weight of the body wash composition. When mixtures of anionic and amphoteric surfactants are used, the ratio of anionic surfactant:amphoteric surfactant can range from about 1:1 to about 15:1 in one aspect, from about 1.5:1 to about 10:1 in another aspect, from about 2.25:1 to about 9:1 in a further aspect, and from about 4.5:1 to about 7:1 in a still further aspect. The amount of the rheology modifier can range from about 0.5 wt. % to about 5 wt. % by weight in one aspect, or from about 1 wt. % to about 3 wt. % of the body wash composition.

The body wash can be formulated as moisturizing body washes, antibacterial body washes, bath gels, shower gels, liquid hand soaps, body scrubs; bubble baths, facial scrubs, foot scrubs, and the like.

Example Shampoo Compositions

In one aspect, a personal care composition in which the rheology modifier is useful is a shampoo. Typical components of a shampoo, in addition to the rheology modifier and water include at least one surfactant a pH adjusting agent (base and/or acid) in sufficient amount to provide a pH of from about 3.0 to about 10 in one aspect, and from about 3.0 to about 7.5 in another aspect; and optional ingredients selected from the additives discussed above, and mixtures thereof, such as conditioning agents (e.g., silicones and/or cationic conditioning agents; small and/or large particle sized silicones), pearlizing agents, vitamins, oils, fragrances, dyes, preservatives including acids, botanicals, and insoluble gas bubbles, liposomes, and cosmetic beads and flakes, and anti-dandruff agents, and mixtures thereof. In one aspect, the surfactant is an anionic surfactant. In another aspect, the surfactant is a mixture of an anionic surfactant and an amphoteric surfactant, in optional combination with a cationic and/or a non-ionic surfactant. In one aspect, the anionic surfactant can be present in an amount ranging from about 5 wt. % to about 40 wt. %, or from about 6 wt. % to about 30 wt. %, or from 8 wt. % to about 25 wt. % of the total weight of the shampoo composition. When mixtures of anionic and amphoteric surfactants are used, the ratio of anionic surfactant to amphoteric surfactant can range from about 1:1 to about 10:1 in one aspect, from about 2.25:1 to about 9:1 in another aspect, and from about 4.5:1 to about 7:1 in a further aspect. The amount of the exemplary rheology modifier can range from about 0.5 wt. % to about 5 wt. % in one aspect, or from about 1 wt. % to about 3 wt. % in another aspect, and from about 1.5 wt. % to about 2.5 wt. % in a further aspect, based on the total weight of the shampoo composition.

Shampoo embodiments can be formulated as 2-in-1 shampoos, baby shampoos, conditioning shampoos, bodifying shampoos, moisturizing shampoos, temporary hair color shampoos, 3-in-1 shampoos, anti-dandruff shampoos, hair color maintenance shampoos, acid (neutralizing) shampoos, medicated shampoos, and salicylic acid shampoos, and the like.

Example Liquid Fatty Acid Soap Based Cleansers

In one aspect, a personal care composition in which the exemplary rheology modifier is useful is a fatty acid soap based cleanser. Typical components of a fatty acid based soap cleanser, in addition to the exemplary rheology modifier include at least one fatty acid salt, an optional surfactant or mixture of surfactants, a pH adjusting agent (base and/or acid) in sufficient amount to provide a pH of above 7 in one aspect, from about 7.5 to about 14 in another aspect, from about 8 to about 13 in still another aspect, and optional ingredients selected from the additives discussed above, and mixtures thereof, including additives selected from silicones, humectants, pearlizing agents, vitamins, oils, fragrances, dyes, preservatives, botanicals, anti-dandruff agents, exfoliating agents, insoluble gas bubbles, liposomes, microsponges, cosmetic beads and flakes.

In one aspect, the fatty acid soaps are selected from at least one the fatty acid salt (e.g., sodium, potassium, or ammonium salt) containing from about 8 to about 22 carbon atoms. In another aspect, the liquid soap composition contains at least one fatty acid salt containing from about 12 to about 18 carbon atoms. The fatty acids utilized in the soaps can be saturated and/or unsaturated and can be derived from synthetic sources, as well as from the saponification of fats and natural oils by a suitable base (e.g., sodium, potassium and ammonium hydroxides). Exemplary saturated fatty acids include octanoic, decanoic, lauric, myristic, pentadecanoic, palmitic, margaric, steric, isostearic, nonadecanoic, arachidic, behenic, and the like, and mixtures thereof. Exemplary unsaturated fatty acids include the salts (e.g., sodium, potassium, ammonium) of myristoleic, palmitoleic, oleic, linoleic, linolenic, and the like, and mixtures thereof. The fatty acids can be derived from animal fat such as tallow or from vegetable oil such as coconut oil, red oil, palm kernel oil, palm oil, cottonseed oil, olive oil, soybean oil, peanut oil, corn oil, and mixtures thereof. The amount of fatty acid soap that can be employed in the liquid cleansing compositions of this embodiment ranges from about 1 wt. % to about 50 wt. % in one aspect, or from about 10 wt. % to about 35 wt. %, or from about 12 wt. % to 25 wt. % of the total composition.

An optional anionic surfactant can be present in the soap composition in an amount ranging from about 1 wt. % to about 25 wt. % in one aspect, or from about 5 wt. % to about 20 wt. %, or from 8 wt. % to about 15 wt. %, based on the total weight of the soap composition. Mixtures of anionic and amphoteric surfactants can be used. The ratio of anionic surfactant to amphoteric surfactant can range from about 1:1 to about 10:1 in one aspect, or from about 2.25:1 to about 9:1, or from about 4.5:1 to about 7:1.

The amount of the exemplary rheology modifier in the liquid soap composition can range from about 0.5 wt. % to about 5 wt. %, or from about 1 wt. % to about 3 wt. %, or from about 1.5 wt. % to about 2.5 wt. %, based on the total weight of the soap composition.

The exemplary liquid fatty acid soap based cleanser embodiments can be formulated as body washes, bath gels, shower gels, liquid hand soaps, body scrubs, bubble baths, facial scrubs, and foot scrubs, 2-in-1 shampoos, baby shampoos, conditioning shampoos, bodifying shampoos, moisturizing shampoos, temporary hair color shampoos, 3-in-1 shampoos, anti-dandruff shampoos, hair color maintenance shampoos, acid (neutralizing) shampoos, anti-dandruff shampoos, medicated shampoos, and salicylic acid shampoos, and the like.

Without intending to limit the scope of the exemplary embodiment, the following examples demonstrate methods of preparing the exemplary rheology modifier and the effectiveness of the rheology modifier as a thickener in an aqueous surfactant-based composition.

EXAMPLES

Materials

Methyl glucoside (MeG) was supplied by Lubrizol Corp, Cleveland, Ohio, USA, in a 60 wt. % active formulation with a purity of the monosaccharide form of greater than 95 wt. %.

An approximately equimolar mixture of caprylate and caprate methyl esters (CC) was obtained from P&G under the tradename CE-810 (50-58% $C_8$, 34-50% $C_{10}$, <2% others).

A plant-based methyl oleate ester (O), a mixture of $C_{13}$-$C_{22}$ long chain methyl fatty esters, predominantly $C_{18}$ (>75% $C_{18}$), was obtained from PMC Group under the tradename Kemester 205.

The following surfactants were supplied by Lubrizol Advanced Materials, Inc., Cleveland, Ohio, USA: sodium laureth sulfate with 2 moles of ethoxylation (SLES2EO); cocamidopropyl betaine (CAPB), under the tradename Chembetaine CAD; sodium lauryl sulfate (SLS), an anionic surfactant; cocobetaine, a zwitterionic surfactant, cocamidopropyl betaine, sodium cocoamphoacetate (SCAA), disodium lauryl sulfosuccinate (DSLSS).

Sodium C14-16 olefin sulfonate (SOS) under the tradename Bio-Terge® AS-40 CG, containing about 39% actives, was obtained from Stepan Products.

Sodium alpha sulfomethyl C12-18 ester and fatty acid salt (AOS), containing 47% solids (about 38% actives, predominantly sodium methyl 2-sulfolaurate and disodium 2-sulfolaurate), under the tradename Alpha-Step® MC-48 was obtained from Stepan Products.

In the weight ratios for surfactants given below, the weight of the respective active is considered.

Test Methods

Except when indicated, the measurement of all the properties in the example formulations was performed on 24 hours, room temperature aged formulations.

Viscosity (in mPa·s) is measured with a DV-II+ Pro Brookfield viscometer (Brookfield Engineering Laboratories, Inc.) and spindle SC421/13R, rotating at 20 rpm; at 20° C.±1° C., according to Brookfield Engineering Manual M/98-161-I496.

The turbidity of the solutions is measured using a Micro100 Turbidimeter (or by Micro100 Turbidimeter), HF Scientific Inc., USA. The turbidity is recorded in Nefelometric Turbidity Units, NTU.

The pH of the compositions is measured at ambient conditions using a conventional pH meter calibrated with pH 4, 7 and 10 standards.

H-1 NMR spectra were obtained in Pyridine-$D_5$ at room temperature on a Bruker AV-500 NMR spectrometer operating at 500.13 MHz for proton detection. A 30 degree pulse width is used for excitation with a repetition rate of 3.93 seconds. 64 scans are usually acquired. The sample solutions are made at a concentration of 25-50 mg/0.5 mL.

1. Preparation of Example Esters

Example A

Preparation of Methyl Glucose Caprylate/Caprate/Oleate (MeG-CCO)

A 250 mL, 4-neck round bottom flask equipped with a mechanical stirrer, a thermometer, a nitrogen inlet, and a Dean Stark trap with a vertical condenser on top is charged with 100 grams methyl glucoside (60 wt. % aqueous solution), 50 grams methyl caprylate/caprate, 30 grams plant-based methyl oleate (as described above, referred to herein simply as methyl oleate) and 0.5 grams sodium carbonate (soda ash). The mixture is stirred and heated under nitrogen atmosphere to 105° C. and the distillate is collected in the Dean Stark trap. The heating is continued. The bottom layer containing water and methanol in the Dean Stark trap is drained to remove these while the top layer containing mostly methyl caprylate/caprylate is conducted back to the reaction mixture. The reaction is held at 160° C. for 24 hours, until the methyl oleate is less than 0.5 wt. % and the methyl caprylate/caprate is less than 0.5 wt. %, as determined by gas chromatography (GC). Vacuum is pulled to <5.0 mmHg and held for 2 hours at 160° C. to distill the unreacted methyl caprylate/caprate and methyl oleate. The remaining viscous liquid is cooled to 80° C. and filtered through a 100 micron bag. H-NMR (solvent: pyridine-d5) reveals the total degree of esterification as 1.01 (0.63 eq. of MeG caprylate/caprate and 0.38 eq. of MeG oleate). The distillate collected by the Dean Stark trap including 12 mL top organic layer is discarded.

Examples B-G

Preparation of Methyl Glucose Caprylate/Caprate/Oleate (MeG-CCO)

The products are synthesized by the method described for Example A above, with the raw material charges according to Table 1. H-NMR results are listed in Table 2.

Example H

Preparation of Methyl Glucose Caprylate/Caprate/Laurate (MeG-CCL)

The product is synthesized by the method described for Example A above, with the raw material charges according to Table 1. H-NMR results are listed in Table 2. The total degree of esterification is 1.02, but the equivalents of MeG Caprylate/Caprate and MeG Laurate were difficult to distinguish.

Example I

Preparation of Methyl Glucose Laurate/Oleate (MeG-LO)

The product is synthesized by the method described for Example A above, with the raw material charges according to Table 1. H-NMR results are listed in Table 2.

Example J

Preparation of Methyl Glucose Caprylate/Caprate (MeG-CC)

The product is synthesized by the method described for Example A above, with the raw material charges according to Table 1. H-NMR results are listed in Table 2.

Examples K and L

Preparation of Methyl Glucose Laurate (MeG-L)

The methyl glucose laurate is synthesized by the method described for Example A above, with the raw material charges according to Table 1. H-NMR results are listed in Table 2.

Example M

Preparation of Methyl Glucose Oleate (MeG-O)

The methyl glucose oleate is synthesized by the method described for Example A above with the raw material charges according to Table 1. H-NMR results are listed in Table 2.

Example N

Preparation of Methyl Glucose Isostearate (MeG I)

The methyl glucose isostearate is synthesized by the method described for Example A above with the raw material charges according to Table 1. H-NMR results are listed in Table 2.

TABLE 1

Formulations for Example Esters

| EX. | Product Name | MeG (60%) | Methyl CC | Methyl Laurate | Methyl Isostearate | Methyl Oleate |
|---|---|---|---|---|---|---|
| A | MeG-CCO | 100 | 50 | | | 30 |
| B | MeG-CCO | 200 | 90 | | | 50 |
| C | MeG-CCO | 200 | 100 | | | 60 |
| D | MeG-CCO | 200 | 74 | | | 58 |
| E | MeG-CCO | 200 | 94 | | | 29 |
| F | MeG-CCO | 200 | 102 | | | 14 |
| G | MeG-CCO | 400 | 148 | | | 116 |
| H | MeG-CCL | 200 | 53 | 66 | | |
| I* | MeG-LO | 200 | | 90 | | 56 |
| J* | MeG-CC | 200 | 120 | | | |
| K* | MeG-L | 400 | | 300 | | |
| L* | MeG-L | 200 | | 150 | | |
| M* | MeG-O | 360 | | | | 334 |
| N | MeG I | 60 | | | 60 | |
| O | MeG-CCO | 200 | 82 | | | 50 |
| P | MeG-CCO | 180 | 83 | | | 65 |
| Q | MeG-CCO | 165 | 91 | | | 72 |
| R* | MeG-L | 225 | | 175 | | |

*Comparative

Table 2 shows the products obtained. Total DS (Degree of Substitution or Degree of Esterification) is the sum of all alkylates on methyl glucoside or the molar ratio of ester:MeG.

TABLE 2

Equivalents of Various Alkyl Esters on MeG

| Example | Product MeG alkylate | Equivalents of Alkyl Esters on MeG, determined by H-NMR | | | | |
|---|---|---|---|---|---|---|
| | | CC | Laurate | Oleate | Iso-stearate | Total DS |
| A | MeG-CCO | 0.63 | | 0.38 | | 1.01 |
| B | MeG-CCO | 0.79 | | 0.30 | | 1.09 |
| C | MeG-CCO | 0.89 | | 0.37 | | 1.26 |
| D | MeG-CCO | 0.69 | | 0.33 | | 1.02 |
| E | MeG-CCO | 0.87 | | 0.19 | | 1.06 |
| F | MeG-CCO | 0.95 | | 0.10 | | 1.05 |
| G | MeG-CCO | 0.67 | | 0.35 | | 1.02 |
| H | MeG-CCL | CC and L not distinguishable | | | | 1.02 |
| I* | MeG-LO | | 0.69 | 0.34 | | 1.03 |
| J* | MeG-CC | 1.05 | | | | 1.05 |
| K* | MeG-L | | 1.12 | | | 1.12 |
| L* | MeG-L | | 1.17 | | | 1.17 |
| M* | MeG-O | | | 1.10 | | 1.10 |
| N* | MeG-I | | | | 1.13 | 1.13 |
| O | MeG-CCO | 0.67 | | 0.29 | | 0.96 |
| P | MeG-CCO | 0.81 | | 0.44 | | 1.25 |
| Q | MeG-CCO | 0.93 | | 0.52 | | 1.45 |
| R* | MeG-L | | 0.92 | | | 0.92 |

*Comparative

2. Preparation and Evaluation of Example Thickening Compositions

Example aqueous surfactant compositions are prepared by thickening a 12 wt. & surfactant mixture composed of SLES2EO/CAPB/salt: in a ratio of 10:2:1 by weight, at pH 5.5. In all these examples a 2.0 wt. % of MeG-alkyl ester thickener is used. The salt used was sodium chloride. The balance of the composition was water.

The thickened surfactant compositions are prepared as follows: in a suitable formulation vessel, at room temperature, using a simple mechanical paddle mixer, water and the MeG-Alkyl ester are mixed to obtain a milky dispersion. SLES2EO and CAPB surfactants are weighed in and mixed until a homogeneous, clear liquid is obtained. Finally, 1.0 wt. % of sodium chloride salt is added and the pH adjusted to 5.5 with citric acid. The short carbon chain ester used in forming the MeG-alkyl ester is an equimolar mixture of caprylate and caprate esters, CC, and the long carbon chain is the oleate ester, O. The reaction conditions and the chemical composition of these esters are as noted above.

TABLE 3 demonstrates the surfactant thickening properties of the example fatty acid esters of methyl glucoside where a combination of short and long carbon chain acids are used to prepare the thickener. The data in the table shows the thickening efficiency of MeG-CCO esters as a function of increasing the content of oleate ester from 0 to 0.52 equivalents in the thickener.

TABLE 3

Surfactant Compositions

| Example No | Chemical Composition | Short Carbon Chain Acid: CC Equivalents | Long Carbon Chain Acid: O Equivalents | Shampoo Turbidity at RT NTU | Visc 20 rpm at 20° C.* mPa·s | O/CC eq/eq |
|---|---|---|---|---|---|---|
| 1** | MeG-CC (Ex J) | 1.05 | 0.00 | 4.20 | 3,200 | 0.00 |
| 2 | MeG-CCO (Ex F) | 0.95 | 0.10 | 3.39 | 3,375 | 0.11 |
| 3 | MeG-CCO (Ex E) | 0.87 | 0.19 | 3.57 | 1,675 | 0.22 |
| 4 | MeG-CCO (Ex B) | 0.79 | 0.30 | 12.79 | 7,412 | 0.38 |
| 5 | MeG-CCO (Ex O) | 0.69 | 0.29 | 14.02 | 3,050 | 0.42 |
| 6 | MeG-CCO (Ex C) | 0.89 | 0.37 | 60.00 | 7,800 | 0.42 |
| 7 | MeG-CCO (Ex D) | 0.69 | 0.33 | 3.68 | 7,337 | 0.48 |
| 8 | MeG-CCO (Ex P) | 0.81 | 0.44 | 24.20 | 7,450 | 0.54 |
| 9 | MeG-CCO (Ex Q) | 0.93 | 0.52 | 43.25 | 8,300 | 0.56 |
| 10 | MeG-CCO (Ex A) | 0.63 | 0.38 | 9.42 | 6,037 | 0.60 |

*Viscosity measured at 20° C., on formulations aged at room temperature for 24 hours.
**Comparative The data in TABLE 3 indicates that as the ratio of oleate to caprylate-caprate equivalents (O/CC) increases, the viscosity of the aqueous surfactant composition tends to increase significantly. It can also be seen that as the O/CC ratio increases the clarity of the formulation tends to drop. Further, increases in the level of oleate or any other long carbon fatty acid ester do not continue improving the viscosity of the surfactant compositions. Both the O/CC ratio and degree of substitution appear to have an effect on the surfactant composition.

Examples 11 to 15 are surfactant compositions where various types of MeG esters of long carbon chain fatty acids are added to the composition to evaluate their overall thickening efficiency and performance. These formulations are prepared as for Examples 1-10 (with 12 wt. % surfactant mixture composed of SLES2EO/CAPB/salt: in a ratio of 10:2:1 by weight, at pH 5.5), except that no short carbon chain fatty acids were used in these examples. TABLE 4 indicates that only a low viscosifying effect is obtained. Additionally, as the level of longer chain fatty acid increases there is a significant drop in the clarity of the formulations.

Most of these compositions are very hazy or simply milky opaque liquids. Mixing the compositions at 55° C. did not improve their viscosity or appearance. They all phase separated in a few hours while standing at ambient conditions.

TABLE 4

Surfactant Compositions with longer chain MeG alkyl ester

| Example No. | MeG - Alkyl ester | Short Carbon Chain Acid | Long Carbon Chain Acid | Shampoo Turbidity @ RT | Viscosity 20 rpm at 20° C. |
|---|---|---|---|---|---|
| | | | Equivalents (degree of substitution) | NTU | |
| 11* | MeG monooleate (Ex K) | no | 1.10 | 398.13 | 1,200 |
| 12* | MeG mono-isosterate (Ex. M) | no | 1.13 | 112.00 | 320 |
| 13* | MeG-LO (Ex L) | no | 0.69/0.34 | 98.29 | 2,500 |
| 14* | MeG-dioleate (Glucate™ dioleate emulsifier) | no | 2.00 | >500 | 30 |
| 15* | MeG-sesquistearate (Glucate™ sequistearate emulsifier) | no | 1.5 | >500 | 30 |

*Comparative

Viscosity Comparison of the Long Term Stability of Surfactant Compositions

Surfactant formulations are generally expected to exhibit stable behavior for extended periods of time. Suitable thickeners used to prepare surfactant compositions should therefore deliver stable properties upon aging. TABLE 5 shows the viscosity and clarity variations of the aqueous surfactant compositions prepared with SLES2EO/CAPB/salt in the ratios 10:2:1, which are thickened with different MeG alkyl esters.

In these experiments, the viscosity and the clarity of the formulation are measured at 20° C. after aging the compositions at room temperature for one hour (freshly made), at 24 hours, and after one month. The data in TABLE 5 indicates that the MeG-CC thickener experienced an almost 70% loss in viscosity in one day of aging. Comparatively, MeG-CCO thickeners exhibit small variations in viscosity upon aging, even after a month. Similarly, the viscosity of the compositions thickened with MeG-monolaurate remains relatively stable after a month, although their clarity continues to be poor, relative to compositions thickened with MeG-CCO.

While the mechanism for the lack of stability of the MeG-CC compositions is not well understood, it may be due to complex interactions with the surfactant molecules which may give raise to phase changes in solution or even some degradation of the thickener.

This suggests that thickeners made from a mixture of short and long fatty acid esters of methyl glucoside such as MeG-CCO can offer a desirable combination of performance properties in surfactant compositions.

TABLE 5

Aging Tests on Surfactant Compositions

| Example No. | MeG Alkyl ester | Viscosity 1 hr mPa·s | Viscosity 24 hr mPa·s | Viscosity 1 Month mPa·s | Turbidity 1 hr NTU | Turbidity 24 hr NTU | Turbidity 1 month NTU |
|---|---|---|---|---|---|---|---|
| 16 | MeG-CC (Ex. G) | 10,100 | 3,200 | 2200 | 4.80 | 4.20 | 4.20 |
| 17 | MeG-CCO (Ex. D) | 7,540 | 7,337 | 6800 | 4.20 | 3.68 | 4.40 |
| 18 | MeG-CCO (Ex. C) | 7910 | 7800 | 7850 | 55.0 | 60.0 | 32.0 |
| 19* | MeG-L (Ex. R) | 7,500 | 7,225 | 6012 | >500 | >500 | 300 |
| 20* | MeG-L (Ex. K) | 6,320 | 6,725 | 5900 | >500 | >500 | 320 |

*Comparative

3. Examples of Shampoo Compositions

Examples 21 to 30 shown in TABLE 6 are aqueous surfactant compositions which are prepared by thickening a 14 wt. % surfactant mixture composed of SLES2EO/CAPB at a ratio of 10:4, at pH 5.7. In these examples various levels of the MeG-CCO thickener of Example A are added. The preparation of the thickened surfactant composition is as follows: in a suitable formulation vessel, at room temperature, using a simple mechanical paddle mixer, water and the MeG-Alkyl ester are mixed to obtain a milky dispersion. SLES2EO and CAPB surfactants are weighed in and mixed until a homogeneous, clear liquid is obtained. Examples 21 to 25 are prepared without the use of salt. Examples 26 to 30 are prepared with sodium chloride salt. The pH is adjusted with citric acid.

The compositions achieved viscosity of greater than 2000 mPa·s at greater than 3 wt. % thickener. However, when a small amount of NaCl is added to the compositions, significant gains in viscosity are achieved, as illustrated in Examples 31 to 35. In this case, a viscosity of greater than 2000 mPa·s can be achieved at MeG-CCO concentrations of ~2 wt. %. The examples in TABLE 6 demonstrate the salt compatibility and synergistic properties of MeG-CCO with electrolytes.

TABLE 6

Effect of MeG-CCO and Salt on Surfactant Compositions

| Example No. | MeG-CCO wt. % | NaCl wt. % | Turbidity, NTU | Viscosity, mPa·s at 20 rpm |
|---|---|---|---|---|
| 21 | 0 | 0 | 5 | 100 |
| 22 | 1 | 0 | 5 | 200 |
| 23 | 2 | 0 | 5 | 387 |
| 24 | 3 | 0 | 5 | 1,975 |
| 25 | 4 | 0 | 5.5 | 5,087 |
| 26 | 0 | 0.20 | 5 | 100 |
| 27 | 1 | 0.20 | 5 | 462 |
| 28 | 2 | 0.20 | 5 | 3,275 |
| 29 | 3 | 0.20 | 5 | 5,837 |
| 30 | 4 | 0.20 | 5 | 8,650 |

4. Examples of Peg-Free Shampoo or Body Wash Compositions

Examples 31 to 36 in TABLE 7 are aqueous surfactant compositions which are prepared by thickening a 14 wt. % surfactant mixture composed of SLS/CAPB: at a weight ratio of 10:4, at pH 5.7. In these examples various levels of the MeG-CCO thickener of Example A are added. The preparation of the thickened surfactant composition is as follows: in suitable formulation vessel, at room temperature, using a simple mechanical paddle mixer, water and the MeG-Alkyl ester are mixed to obtain a milky dispersion. SLS and CAPB surfactants are weighed in and mixed until a homogeneous, clear liquid is obtained. In these examples, sodium chloride salt is not added, although it is to be appreciated that sodium chloride salt may be added and the pH adjusted with an acid (e.g., citric acid).

Examples 31 to 36 demonstrate the thickening efficiency of MeG-CCO in the SLS (anionic surfactant)/CAPB surfactant system. Clear compositions and viscosities of greater than 2000 mPa·s are easily achieved at ~0.25 wt. % of the thickener and the compositions did not require salt. At 2 wt. % of thickener the formulation became milky and exhibited a loss of viscosity. As will be appreciated, preparation of detailed concentration and salt curves could be performed to adjust the final viscosity of the composition during formulation development and processing.

TABLE 7

PEG-free Surfactant Compositions With Anionic Surfactant

| Example No. | MeG-CCO wt. % | NaCl wt. % | Turbidity, NTU | Viscosity, mPa·s at 20 rpm |
|---|---|---|---|---|
| 31 | 0 | 0 | 4 | 100 |
| 32 | 0.25 | 0 | 5 | 1,887 |
| 33 | 0.5 | 0 | 5 | 2,850 |
| 34 | 0.75 | 0 | 5 | 2,625 |
| 35 | 1.00 | 0 | 5.5 | 25,000 |
| 36 | 2.00 | 0 | >500 | 100 |

5. Examples of Peg-Free, Green Shampoo and Body Wash Compositions

Examples 37 to 41 in TABLE 8 are aqueous surfactant compositions which are prepared by thickening a 12 wt. % surfactant mixture of PEG-free, renewable or green surfactants composed of SLS/Cocobetaine at a weight ratio of 10:2, at pH 5.5.

In these examples, various levels of the MeG-CCO thickener of Example D are added. The preparation of the thickened surfactant composition is as follows: in a suitable formulation vessel, at room temperature, using a simple mechanical paddle mixer, water (q. s. to 100) and the MeG-Alkyl ester are mixed to obtain a milky dispersion. SLS and cocobetaine surfactants are weighed in and mixed until a homogeneous, clear liquid is obtained. Optionally, sodium chloride salt is added and the pH adjusted with citric acid.

Examples 37 to 41 demonstrate the thickening efficiency of MeG-CCO in the SLS/CAPB surfactant system. Clear compositions with viscosities of greater than 2000 mPa·s were easily achieved at various concentrations of the thickener. The examples also demonstrate the high versatility of the MeG-CCO thickener to achieve clear and highly viscous compositions as desired by simply adjusting the concentration of thickener and salt.

TABLE 8

PEG-free, Green Surfactant System with Anionic and Zwitterionic Surfactants

| Example No. | MeG-CCO wt. % | NaCl wt. % | Turbidity, NTU | Viscosity, mPa · s at 20 rpm |
|---|---|---|---|---|
| 37 | 0 | 1.0 | 5.00 | 100 |
| 38 | 1.0 | 1.0 | 3.00 | 5,987 |
| 39 | 1.0 | 2.0 | 7.27 | 12,325 |
| 40 | 2.0 | 1.0 | 10.00 | 10,462.0 |
| 41 | 3.0 | 0.5 | 4.32 | 10,937 |

6. Examples of Peg-Free, Sulfate Free, Green Shampoo and Body Wash Compositions Examples 42 to 44 in TABLE 9 are aqueous surfactant compositions which were prepared by thickening a mixture of sulfate free surfactants at 14 wt. % total surfactant. The mixture is composed of SCAA/CAPB/DSLSS in a weight ratio of 5:5:4 at pH 5.45. In these examples MeG-CCO thickener was added at 1%. The thickener used in these compositions was an MeG-CCO formed analogously to Example B.

The preparation of the thickened surfactant composition was as follows: in a suitable formulation vessel, at room temperature, using a simple mechanical paddle mixer, water and the MeG-Alkyl ester were mixed to obtain a milky dispersion. SCAA, CAPB and DSLSS were weighed in and mixed until a homogeneous, clear liquid was obtained. Optionally, sodium chloride salt may be added and the pH adjusted with citric acid.

Example 42 is an example of a clear and viscous sulfate free cleansing formulation. Example 43 is a pearlescent formulation which uses gold mica to achieve the effect. This formulation is stable at a high temperature (45° C.) for one month. Example 44 is a sulfate free pearlescent formulation which uses a water dispersion of ethylene glycol distearate to achieve the effect. This formulation is stable for three months at high temperature (45° C.). TABLE 9 shows the parts by weight, the formulations are made up to 100 parts with DI water. None of these formulations require the use of salt to achieve viscosity of greater than 2,000 mPa·s.

7. Example of Peg-Free and Sulfate-Free Body Wash

Example 45 is an example of a PEG-free and Sulfate-free Body Wash containing a surfactant system of SOS/CAPB/AOS at 19.4% in a weight ratio of 12:5.25:2.15, prepared as described above.

TABLE 11

PEG-free and Sulfate-free Body Wash (Example 45)

| Ingredient | Active parts | % Activity | pph |
|---|---|---|---|
| Sodium C14-16 olefin sulfonate (SOS) | 12 | 39.0 | 30.77 |
| CAPB | 5.25 | 35.0 | 15.00 |
| Sodium alpha sulfomethyl C12-18 (AOS) | 2.15 | 47.0 | 4.62 |
| MeG - CCO (Ex. B) | 2.00 | 100.0 | 2.11 |
| NaCl | 1.00 | 100 | 1.00 |
| Citric acid | | 25 | — |
| Water | | | 46.50 |
| TOTAL | | | 100.00 |
| Turbidity, NTU | 6.37 | | |
| Viscosity, mPa · s at 20 rpm | 11,475 | | |

Each of the documents referred to herein is incorporated herein by reference, in its entirety.

Except in the Examples, or where otherwise explicitly indicated, all numerical quantities in this description specifying amounts of materials, reaction conditions, molecular weights, number of carbon atoms, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

As used herein, the expression "consisting essentially of" permits the inclusion of substances that do not materially affect the basic and novel characteristics of the composition under consideration.

As used herein, the expression "consisting of" permits the inclusion of only the elements listed therein, except as present as a result of impurities in the materials used as reagents.

"Predominantly," as used herein, means greater than 60%, or greater than 80%, or greater than 90%.

TABLE 9

PEG-free, Sulfate Free, Green Surfactant Compositions

| Example No. | MeG-CCO | Mica | Quick Pearl | FD&C Blue #1 Dye (0.1% solution) | Germall II Preservative | Turbidity (NTU) | Viscosity, mPa · s at 20 rpm |
|---|---|---|---|---|---|---|---|
| 42 | 1.00 | | | | | 8.2 | 9,000 |
| 43 | 1.00 | 0.10 | | 0.1 | 0.25 | na | 6,850 |
| 44 | 2.00 | | 2.00 | | 0.25 | na | 3,200 |

The polymers and compositions disclosed herein may suitably comprise, consist of, or consist essentially of the components, elements, and process delineations described herein. The polymers and compositions disclosed herein illustratively disclosed herein suitably may be formed in the absence of any element which is not specifically disclosed herein.

Unless otherwise stated, all percentages, parts, and ratios expressed herein are based upon weight of the total composition.

As used herein any member of a genus (or list) may be excluded from the claims.

As used herein, the term "(meth)acrylic" and related terms includes both acrylic and methacrylic groups.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:
1. A composition comprising:
a surfactant;
a rheology modifier comprising a mixture of alkyl glycoside fatty acid esters comprising:
a long chain fatty acid ester of an alkyl glycoside, the long chain fatty acid ester consisting of at least one fatty acid ester group $R^1(O)O$—, wherein $R^1$ is a $C_{12}$ or higher hydrocarbon, and
a short chain fatty acid ester of an alkyl glycoside, the short chain fatty acid ester consisting of least one fatty acid ester group $R^2(O)O$—, wherein $R^2$ is a $C_6$-$C_{10}$ hydrocarbon; and
water,
wherein a molar ratio of long chain fatty acid ester groups to short chain fatty acid ester groups in the rheology modifier is less than 1:1.

2. The composition of claim 1, wherein in the long chain fatty acid ester $R^1$ is a C12-$C_{23}$ hydrocarbon.

3. The composition of claim 1, wherein in the long chain fatty acid ester, $R^1$ is a $C_{13}$ or higher hydrocarbon.

4. The composition of claim 1, wherein the long chain fatty acid comprises at least one fatty acid ester in which $R^1$ is a $C_{18}$ hydrocarbon.

5. The composition of claim 1, wherein the long chain fatty acid ester comprises at least one fatty acid ester in which $R^1$ is an unsaturated hydrocarbon.

6. The composition of claim 1, wherein the long chain fatty acid ester comprises a plant-derived fatty acid ester group derived from at least one of linoleic acid, linolenic acid, oleic acid, stearic acid, and esters thereof.

7. The composition of claim 1, wherein the short chain fatty acid ester comprises at least one fatty acid ester group $R^2(O)O$—, wherein $R^2$ is a $C_8$-$C_{10}$ hydrocarbon.

8. The composition of claim 1, wherein the short chain fatty acid ester comprises at least one plant based fatty acid ester derived from capric and caprylic acids or esters thereof.

9. The composition of claim 1, wherein the short chain fatty acid ester comprises at least one of hexanoate, heptanoate, caprylate, pelargonate, and caprate, of methyl glucoside, and combinations thereof, and the long chain glucoside ester comprises at least one of laurate, myristate palmitate, stearate, isostearate, linoleate, linolenate, oleate, and behenate of methyl glucoside, and combinations thereof.

10. The composition of claim 9, wherein the rheology modifier comprises alkyl glucoside esters derived from caprylic acid, capric acid, and plant-based oleic acid, or their esters.

11. The composition of claim 1, wherein a ratio of long chain fatty acid ester groups to short chain fatty acid ester groups in the rheology modifier is at least 0.1:1.

12. The composition of claim 11, wherein the ratio of long chain fatty acid ester groups to short chain fatty acid ester groups in the rheology modifier is at least 0.2:1.

13. The composition of claim 11, wherein the ratio of long chain fatty acid ester groups to short chain fatty acid ester groups in the rheology modifier is at least 0.3:1.

14. The composition of claim 1, wherein the ratio of long chain fatty acid ester groups to short chain fatty acid ester groups in the rheology modifier is up to 0.8:1.

15. The composition of claim 14, wherein the molar ratio of long chain fatty acid ester to short chain fatty acid ester groups in the rheology modifier is up to 0.7:1.

16. The composition of claim 1, wherein a molar ratio of long chain fatty acid ester groups to short chain fatty acid ester groups in the rheology modifier is 0.2:1 to 0.8:1.

17. The composition of claim 1, wherein the long chain fatty acid ester comprises plant-based oleic ester groups and the short chain fatty acid ester comprises caprylic and capric ester groups and wherein a molar ratio of unsaturated $C_{18}$ ester groups to other ester groups (O/CC ratio) is from 0.2:1 to 0.7:1.

18. The composition of claim 17, wherein the O/CC ratio is from 0.35:1 to 0.6:1.

19. The composition of claim 1, wherein a degree of esterification per molecule of glycoside is from 0.7:1 to 1.5:1.

20. The composition of claim 19, wherein the degree of esterification is from 0.8:1 to 1.2:1.

21. The composition of claim 1, wherein the alkyl glycoside comprises an alkyl glucoside.

22. The composition of claim 21, wherein the alkyl glucoside is a $C_1$-$C_{30}$ alkyl glucoside.

23. The composition of claim 22, wherein the alkyl glucoside comprises methyl glucoside.

24. The composition of claim 1, wherein the alkyl glycoside fatty acid esters have a molecular weight of less than 1000.

25. The composition of claim 1, further comprising a non-aqueous solvent.

26. The composition of claim 1, wherein the rheology modifier increased the viscosity of the composition by a factor of at least 10 when the alkyl glycoside fatty acid esters are at a total concentration of up to 4 wt. % of the surfactant composition, as compared to an otherwise identical composition without the rheology modifier.

27. The composition of claim 1, wherein none of the alkyl glycoside fatty acid esters in the rheology modifier is alkoxylated.

28. The composition of claim 1, wherein the rheology modifier is present at a concentration of at least 0.1 wt. %.

29. The composition of claim 28, wherein the rheology modifier is present at a concentration of at least 0.5 wt. %.

30. The composition of claim 29, wherein the rheology modifier is present at a concentration of at least 1 wt. %.

31. The composition of claim 1, wherein the rheology modifier is present at a concentration of up to 5 wt. %.

32. The composition of claim 31, wherein the rheology modifier is present at a concentration of up to 3 wt. %.

33. The composition of claim 1, wherein the surfactant is present at a concentration of at least 0.01 wt. %.

34. The composition of claim 32, wherein the surfactant is present at a concentration of at least 1 wt. %.

35. The composition of claim 1, wherein the surfactant is present at a concentration of up to 20 wt. %.

36. The composition of claim 1, wherein a ratio by weight of the alkyl glycoside fatty acid esters to the surfactant is less than 1:1.

37. The composition of claim 1, wherein a ratio by weight of the alkyl glycoside fatty acid esters to the surfactant is up to 0.5:1.

38. The composition of claim 1, wherein the surfactant comprises an anionic surfactant.

39. The composition of claim 38, wherein the surfactant further comprises a zwitterionic surfactant.

40. The composition of claim 1, wherein the composition is free of alkoxylated surfactants.

41. The composition of claim 1, wherein the composition is free of sulfate based surfactants.

42. The composition of claim 1, wherein the rheology modifier is not alkoxylated.

43. The composition of claim 1, further comprising at least 0.1% of a salt selected from soluble inorganic salts and organic salts having a molecular weight of less than 300.

44. The composition of claim 43, wherein the salt comprises a soluble inorganic salt.

45. The composition of claim 44, wherein composition comprises at least 0.2% of the soluble inorganic salt.

46. The composition of claim 1, wherein the composition comprises at least 40 wt. % water.

47. The composition of claim 1, wherein the composition has a viscosity of at least 1000 mPa s, when measured at 24 hours after formation of the composition.

48. The composition of claim 47, wherein the composition has a viscosity of at least 2000 mPa s, measured at 20° C., 24 hours after formation of the composition.

49. The composition of claim 47, wherein the composition has a viscosity of up to 10,000 mPa s, measured at 20° C., 24 hours after formation of the composition.

50. The composition of claim 1, wherein the composition has a turbidity of less than 60 NTU, measured at 24 hours after formation of the composition.

51. The composition of claim 50, wherein the composition has a turbidity of less than 30 NTU, at 24 hours after formation.

52. The composition of claim 1, wherein the composition is formed by mixing the surfactant and rheology modifier with water at ambient temperature.

53. The composition of claim 1, further comprising at least one of silicones, emollients, silicones, emulsifiers, pearlescent agents, coloring agents, particulates, preservatives, pH adjusting agents, botanicals, chelating agents, antimicrobials, and auxiliary rheology modifiers.

54. The composition of claim 1, wherein the composition is formulated for a personal care application selected from a shampoo, a body wash, a liquid soap, a facial cleanser, and a hand soap.

55. A method of forming the composition of claim 1 comprising:

combining a rheology modifier with a surfactant and water, the rheology modifier comprising a mixture of alkyl glycoside fatty acid esters comprising:
a long chain fatty acid ester of an alkyl glycoside, the long chain fatty acid ester consists of at least one fatty acid ester group $R^1(O)O$—, wherein $R^1$ is a C12 or higher hydrocarbon, and
a short chain fatty acid ester of an alkyl glycoside, the short chain fatty acid ester consisting of least one fatty acid ester group: $R^2(O)O$—, wherein $R^2$ is a $C_6$-$C_{10}$ hydrocarbon,
wherein a molar ratio of long chain fatty acid ester groups to short chain fatty acid ester groups in the rheology modifier is less than 1:1.

56. The method of claim 55, wherein the combining is performed at ambient temperature.

57. The method of claim 55, further comprising forming the rheology modifier comprising:
separately or in combination, reacting an alkyl glycoside with a long chain fatty acid of the formula $R^1(O)OH$ or derivative thereof and with a short chain fatty acid of the formula $R^2(O)OH$ or derivative thereof.

58. A rheology modifier comprising a mixture of alkyl glycoside fatty acid esters comprising:
a long chain fatty acid ester of an alkyl glycoside, the long chain fatty acid ester consisting of at least one fatty acid ester group $R^1(O)O$—, wherein $R^1$ is a $C_{12}$-$C_{23}$ hydrocarbon group, and
a short chain fatty acid ester of an alkyl glycoside, the short chain fatty acid ester consisting of least one fatty acid ester group $R^2(O)O$—, wherein $R^2$ is a $C_6$-$C_{10}$ hydrocarbon group; and
wherein a ratio of $R^1(O)O$— to $R^2(O)O$— in the rheology modifier is from 0.2:1 to 0.7:1.

59. The rheology modifier of claim 58, wherein $R^1$ comprises a mixture of $C_8$ and $C_{10}$ hydrocarbon groups derived from caprylic and capric acids or derivatives thereof and $R^2$ comprises a mixture of $C_{18}$ is hydrocarbon groups derived from plant-based oleic acid or derivatives thereof.

60. A composition comprising a rheology modifier derived from a reaction of an alkyl glycoside with a long chain fatty acid or derivative thereof and a short chain fatty acid or derivative thereof, the short and long chain fatty acids or derivatives thereof including a hydrocarbon chain of at least 6 carbons in length, and wherein the short and long chain fatty acids or derivatives thereof differ in the length of their respective hydrocarbon chains by an average of at least 6 carbon atoms, wherein a molar ratio of the long chain fatty acid or derivative thereof to the short chain fatty acid or derivative thereof is less than 1:1.

61. The composition of claim 60, further comprising a surfactant.

62. The composition of claim 60, further comprising water.

63. The composition of claim 61 further comprising water.

* * * * *